United States Patent
Gaspard et al.

(10) Patent No.: US 11,944,112 B2
(45) Date of Patent: Apr. 2, 2024

(54) STABILIZED STEVIOL GLYCOSIDE MALONIC ACID ESTERS

(71) Applicant: CARGILL, INCORPORATED, Wayzata, MN (US)

(72) Inventors: Dan S. Gaspard, Victoria, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 17/823,790

(22) Filed: Aug. 31, 2022

(65) Prior Publication Data

US 2023/0000124 A1     Jan. 5, 2023

Related U.S. Application Data

(63) Continuation of application No. PCT/US2021/028154, filed on Apr. 20, 2021.

(60) Provisional application No. 63/012,591, filed on Apr. 20, 2020.

(51) Int. Cl.
| | |
|---|---|
| A23L 27/30 | (2016.01) |
| A23L 2/60 | (2006.01) |
| A23L 2/68 | (2006.01) |

(52) U.S. Cl.
CPC ............ *A23L 27/36* (2016.08); *A23L 2/60* (2013.01); *A23L 2/68* (2013.01)

(58) Field of Classification Search
CPC ............ A23L 27/36; A23L 2/60; A23L 2/68
See application file for complete search history.

(56) References Cited

U.S. PATENT DOCUMENTS

| | | | |
|---|---|---|---|
| 3,876,816 A * | 4/1975 | Zaffaroni | C07D 303/22 |
| | | | 426/19 |
| 4,404,367 A | 9/1983 | Stephenson | |
| 8,337,927 B2 | 12/2012 | Purkayastha | |
| 9,771,434 B2 | 9/2017 | Markosyan | |
| 2013/0274351 A1 | 10/2013 | Markosyan | |
| 2019/0223481 A1 | 7/2019 | Gaspard | |
| 2019/0223482 A1 | 7/2019 | Gaspard | |
| 2019/0223483 A1 | 7/2019 | Gaspard | |
| 2019/0350242 A1 | 11/2019 | Jackson | |
| 2020/0260767 A1 | 8/2020 | Gaspard | |
| 2020/0268026 A1 | 8/2020 | Khare | |
| 2020/0268027 A1 | 8/2020 | Gaspard | |
| 2021/0378276 A1 | 12/2021 | Gaspard | |
| 2022/0162250 A1 | 5/2022 | Gaspard | |
| 2022/0248719 A1 | 8/2022 | Gaspard | |
| 2022/0323528 A1 | 10/2022 | Gaspard | |
| 2023/0127708 A1 | 4/2023 | Gaspard | |

FOREIGN PATENT DOCUMENTS

| | | |
|---|---|---|
| CN | 103570777 A | 2/2014 |
| CN | 105175462 A | 12/2015 |
| CN | 110372762 A | 10/2019 |
| JP | 5123300 Y2 | 6/1976 |
| WO | 2012068457 A1 | 5/2012 |
| WO | 2015126876 A1 | 8/2015 |
| WO | 2017059414 A1 | 4/2017 |
| WO | 2018102447 A2 | 6/2018 |
| WO | 2019071182 A1 | 4/2019 |
| WO | 2019071187 A1 | 4/2019 |
| WO | 2020210161 A1 | 10/2020 |

OTHER PUBLICATIONS

DuBois, G. E., et al., "Diterpenoid Sweeteners. Synthesis and Sensory Evaluation of Stevioside Analogues with Improved Organoleptic Properties", . Med. Chem. 1985, 28, 93-98.

\* cited by examiner

*Primary Examiner* — Jeffrey P Mornhinweg

(57) ABSTRACT

Various embodiments disclosed relate to stabilized steviol glycoside malonic acid esters and methods of making the same. A composition includes one or more steviol glycoside malonic acid esters (SGMAs) or salts thereof. The composition also includes a stabilizer including one or more caffeoyl-substituted quinic acids or salts thereof. The composition can be a beverage or beverage concentrate having a pH of 1.7 to 4, and/or the composition can have a mass ratio of the one or more SGMAs, salts thereof, or combination thereof to the stabilizer of 1:5 to 3:1.

24 Claims, 1 Drawing Sheet

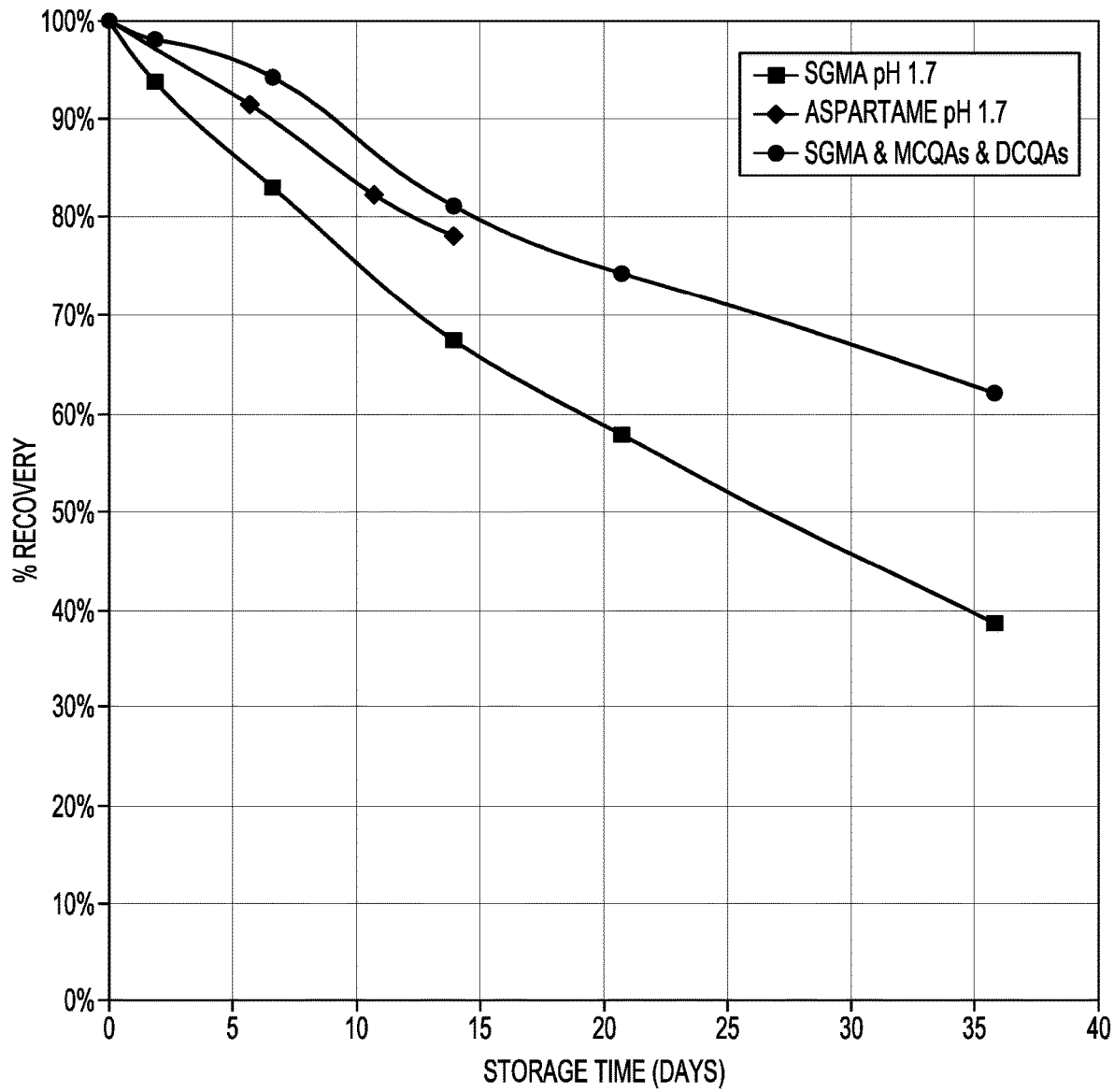

STABILIZED STEVIOL GLYCOSIDE MALONIC ACID ESTERS

CROSS-REFERENCE TO RELATED APPLICATIONS

This application is a Continuation of International Application No. PCT/US2021/028154, filed Apr. 20, 2021, which claims the benefit of U.S. Provisional Patent Application No. 63/012,591, filed Apr. 20, 2020, each of which is hereby incorporated by reference herein in its entirety.

BACKGROUND

In recent decades, consumers have increasingly sought low-calorie alternatives to calorie-rich products. Steviol glycosides offer a non-caloric alternative to traditional caloric sweeteners such as sugar, glucose, sucrose, and/or fructose. Steviol glycosides are a class of sweet-tasting glycosylated diterpene compounds commonly obtained from the leaves of Stevia rebaudiana. Various steviol glycosides are known, some of which provide a sugar-like taste profile and are 150 to 450 times sweeter than sugar. Such compounds are typically characterized by a single steviol backbone and the presence of differing arrangements of glycosidic carbohydrate residues at positions C13 and C19.

Some steviol glycosides can suffer from poor acidic stability on their own, limiting their use in acidic compositions such as carbonated soft drinks or throw syrups.

SUMMARY OF THE INVENTION

In various aspects, the present invention provides a composition including one or more steviol glycoside malonic acid esters (SGMAs) or salts thereof. The composition also includes a stabilizer that includes one or more caffeoyl-substituted quinic acids or salts thereof.

In various aspects, the present invention provides a composition including one or more steviol glycoside malonic acid esters (SGMAs) or salts thereof. The composition also includes a stabilizer including 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, salts thereof, or combinations thereof.

In various aspects, the composition may be a sweetener or a sweetened composition such as a beverage concentrate, a sweetened beverage, a carbonated soft drink, a solid food stuff, a pharmaceutical composition, a nutritional supplement, or a dental composition.

In various aspects, the composition may be a beverage or beverage concentrate having a pH of 1.7 to 4.

In various aspects, the composition has a mass ratio of the one or more SGMAs, salts thereof, or combination thereof to the stabilizer of 1:5 to 3:1.

In various aspects, 0-5% (wt) of the composition may be one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin; or 0-3% (wt) of the composition may be one or more of malonate, malonic acid, oxalate, oxalic acid, lactate, lactic acid, succinate, succinic acid, malate, malic acid, citrate, and citric acid; or 0-1% (wt) of the composition may be one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol; or 0-0.5% (wt) of the composition may be one or more of tartrate, tartaric acid, pyruvate, pyruvic acid, fumarate, fumaric acid, ascorbic acid, sorbate, sorbic acid, acetate, acetic acid, and chlorophyll; or a combination thereof.

In various aspects, the present invention provides a beverage or beverage concentrate including one or more steviol glycoside malonic acid esters (SGMAs) or salts thereof. The beverage or beverage concentrate also includes a stabilizer. The stabilizer includes one or more caffeoyl-substituted quinic acids or salts thereof. The beverage or beverage concentrate has a pH of 1.7 to 4. The beverage or beverage concentrate has a mass ratio of the one or more SGMAs, salts thereof, or combination thereof to the stabilizer of 1:5 to 3:1.

In various aspects, the present invention provides a method of making a composition including one or more steviol glycoside malonic acid esters (SGMAs) or salts thereof, and also including a stabilizer including one or more caffeoyl-substituted quinic acids or salts thereof. The method includes combining the one or more SGMAs, salts thereof, or combination thereof and the stabilizer to form the composition.

In various aspects, the present invention provides a method of making a composition. The method includes combining an SGMA component with a stabilizer component to form the composition. The SGMA component includes at least 30 weight percent on a dry weight basis (wt % dwb) of one or more steviol glycoside malonic acid esters (SGMAs) or salts thereof. The stabilizer component includes at least 30 wt % dwb of one or more caffeoyl-substituted quinic acids or salts thereof.

In various aspects, the present invention provides a method of making a composition including one or more steviol glycoside malonic acid esters (SGMAs) or salts thereof and a stabilizer including one or more caffeoyl-substituted quinic acids or salts thereof. The method includes combining a SGMA component including the one or more SGMAs, salts thereof, or combination thereof with the stabilizer to form the composition including one or more steviol glycoside malonic acid esters (SGMAs) or salts thereof and a stabilizer including one or more caffeoyl-substituted quinic acids or salts thereof. An amount of 0-5% (wt) of the SGMA component may be one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin; or 0-3% (wt) of the SGMA component may be one or more of malonate, malonic acid, oxalate, oxalic acid, lactate, lactic acid, succinate, succinic acid, malate, malic acid, citrate, and citric acid; or 0-1% (wt) of the SGMA component may be one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol; or 0-0.5% (wt) of the SGMA component may be one or more of tartrate, tartaric acid, pyruvate, pyruvic acid, fumarate, fumaric acid, ascorbic acid, sorbate, sorbic acid, acetate, acetic acid, and chlorophyll; or a combination thereof.

Various embodiments of the present invention provide advantages over other compositions including SGMAs and method of making the same. For example, in various embodiments, the composition of the present invention can provide greater SGMA stability under acidic conditions than other SGMA-containing compositions. In various embodiments, the composition of the present invention provides greater stability of SGMAs under acidic conditions than a corresponding composition including aspartame (the most commonly used artificial high-potency sweetener used today) instead of the SGMAs and one or more stabilizers of the composition of the present invention.

SGMAs show promise as sweeteners or flavor modifiers. Unfortunately, they can degrade, particularly at lower pH, limiting their utility in certain applications such as soft drinks, beverage concentrates, and condiments. Compositions disclosed here can increase stability of SGMAs, increasing shelf life of products containing SGMAs. This can be particularly useful in soft drinks, which may be bottled and stored for months, and in liquid water enhancers and throw syrups used to make fountain soft drinks, both of which have to be stored for months under challenging conditions before use.

BRIEF DESCRIPTION OF THE FIGURES

The drawings illustrate generally, by way of example, but not by way of limitation, various embodiments of the present invention.

FIG. 1 illustrates the percent recovery over time in a pH 1.7 solution of aspartame, SGMA, and SGMA including MCQA and DCQA acid stabilizers, according to various embodiments.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In this document, the term "parts per million" or "ppm" means parts per million on a weight basis unless context dictates otherwise.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "hydrocarbon" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

Composition Including SGMAs and Stabilizer.

Various aspects of the present invention provide a composition including one or more steviol glycoside malonic acid esters (SGMAs) or salts thereof. The composition also includes a stabilizer. The composition can improve stability of the SGMAs under acidic conditions, as compared to a corresponding composition that includes less or none of the stabilizer. The composition can improve sweetness quality as compared to a corresponding composition that includes less or none of the stabilizer. The composition can be a sweetener having a relatively high concentration of the SGMAs, salts thereof, or a combination thereof. The composition can be a food product, a sweetened composition, or a beverage with a relatively lower concentration of the SGMAs, salts thereof, or a combination thereof. Compositions that are food products, beverages, or sweetened compositions can be formed from compositions that are sweeteners by combining the sweeteners with other materials.

The composition can be a beverage, such as a carbonated or non-carbonated soft drink, or a beverage concentrate such as a throw syrup, a water enhancer, or a flavored water enhancer, having a pH of 1.7 to 4.

The composition can have a mass ratio of the one or more SGMAs, salts thereof, or combination thereof to the stabilizer of 1:5 to 3:1.

A number of compounds can undesirably impact flavor, aroma, color, or other sensory aspects of the composition. In the interest of limiting or eliminating such compounds, an amount of 0-5% (wt) of the composition can be one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin; or 0-3% (wt) of the composition can be one or more of malonate, malonic acid, oxalate, oxalic acid, lactate, lactic acid, succinate, succinic acid, malate, malic acid, citrate, and citric acid; or 0-1% (wt) of the composition can be one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol; or 0-0.5% (wt) of the composition can be one or more of tartrate, tartaric acid, pyruvate, pyruvic acid, fumarate, fumaric acid, ascorbic acid, sorbate, sorbic acid, acetate, acetic acid, and chlorophyll; or a combination thereof.

The stabilizer can include one or more caffeoyl-substituted quinic acids or salts thereof. The caffeoyl-substituted quinic acids can include an ester derived from the carboxylic acid of caffeic acid and an alcohol of quinic acid. A "caffeoyl-substituted quinic acid" or "caffeoylquinic acid" as the terms are used herein, include monocaffeoylquinic acids, e.g., chlorogenic acid (5-O-caffeoylquinic acid), neochlorogenic acid (3-O-caffeoylquinic acid), and cryptochlorogenic acid (4-O-caffeoylquinic acid), and dicaffeoylquinic acids, e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof. Thus, the stabilizer can include both acid forms and salt forms of caffeoyl-substituted quinic acids.

Chlorogenic acid (5-O-caffeoylquinic acid) has the following structure:

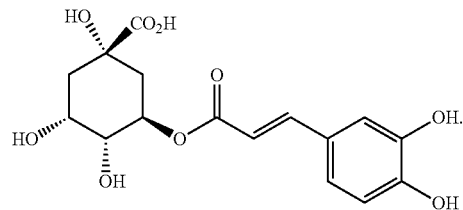 [SMILES: O=C(/C=C/c1ccc(O)c(O)c1)O[C@@H]1C[C@](O)(C(=O)O)C[C@@H](O)[C@H]1O]

Neochlorogenic acid (3-O-caffeoylquinic acid) has the following structure:

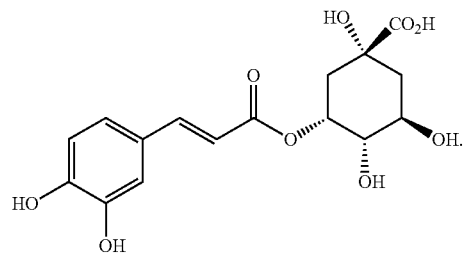 [SMILES: O=C(/C=C/c1ccc(O)c(O)c1)O[C@@H]1C[C@@](O)(C(=O)O)C[C@@H](O)[C@@H]1O]

Cryptochlorogenic acid (4-O-caffeoylquinic acid) has the following structure:

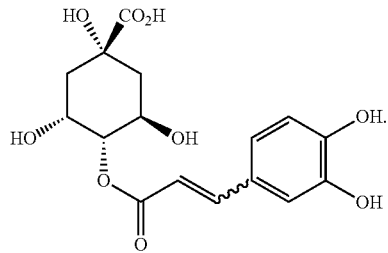 [SMILES: O=C(C=Cc1ccc(O)c(O)c1)O[C@H]1[C@H](O)C[C@](O)(C(=O)O)C[C@H]1O]

1,5-Dicaffeoylquinic acid has the following structure:

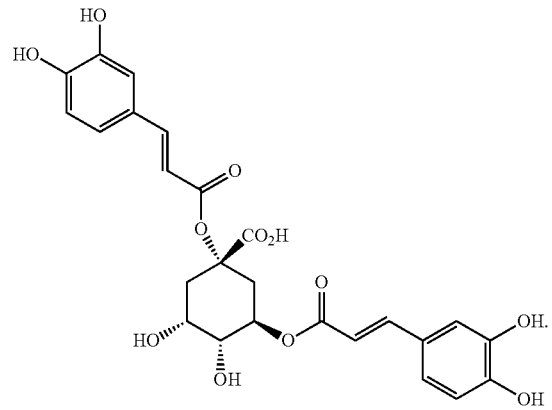 [SMILES: O=C(/C=C/c1ccc(O)c(O)c1)O[C@@H]1C[C@](OC(=O)/C=C/c2ccc(O)c(O)c2)(C(=O)O)C[C@@H](O)[C@H]1O]

3,4-Dicaffeoylquinic acid has the following structure:

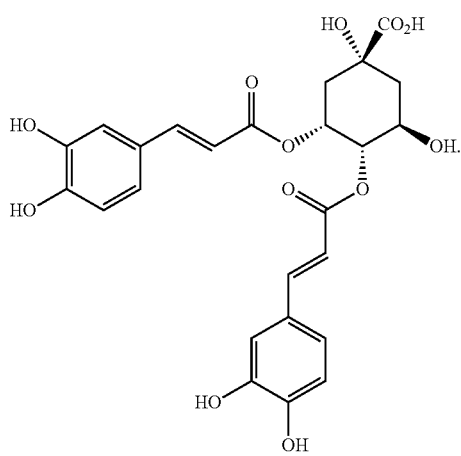 [SMILES: O=C(/C=C/c1ccc(O)c(O)c1)O[C@H]1[C@H](O)C[C@](O)(C(=O)O)C[C@H]1OC(=O)/C=C/c1ccc(O)c(O)c1]

1,3-Dicaffeoylquinic acid has the following structure:

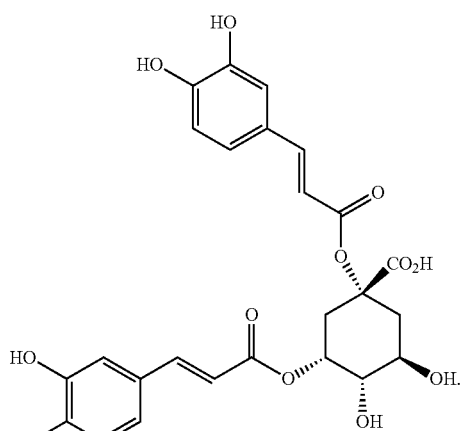

3,5-Dicaffeoylquinic acid has the following structure:

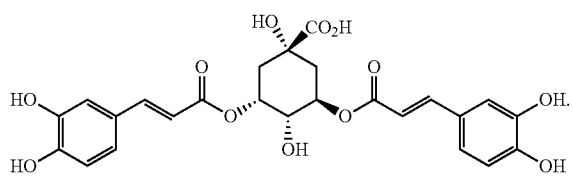 [SMILES: O=C(/C=C/c1ccc(O)c(O)c1)O[C@@H]1C[C@](O)(C(=O)O)C[C@@H](OC(=O)/C=C/c2ccc(O)c(O)c2)[C@H]1O]

1,4-Dicaffeoylquinic acid has the following structure:

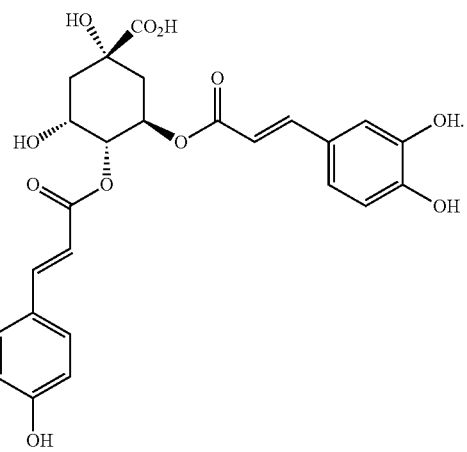

4,5-Dicaffeoylquinic acid has the following structure:

In various aspects, the stabilizer further includes one or more of quinic acid, caffeic acid, ferulic acid, sinapic acid, p-coumaric acid, an ester of quinic acid, an ester of caffeic acid, an ester of ferulic acid, an ester of sinapic acid, an ester of p-coumaric acid, an ester of caffeic acid and quinic acid, an ester of caffeic acid and quinic acid including a single caffeic acid moiety, an ester of caffeic acid and quinic acid including more than one caffeic acid moiety, an ester of ferulic acid and quinic acid, an ester of ferulic acid and quinic acid including a single ferulic acid moiety, an ester of ferulic acid and quinic acid including more than one ferulic acid moiety, an ester of sinapic acid and quinic acid, an ester of sinapic acid and quinic acid including a single sinapic acid moiety, an ester of sinapic acid and quinic acid including more than one sinapic acid moiety, an ester of p-coumaric acid and quinic acid, an ester of p-coumaric acid and quinic acid including a single p-coumaric acid moiety, an ester of p-coumaric acid and quinic acid including more than one p-coumaric acid moiety, a di-ester of quinic acid containing one caffeic acid moiety and one ferulic acid moiety, a caffeic ester of 3-(3,4-dihydroxyphenyl)lactic acid, a caffeic acid ester of tartaric acid, a caffeic acid ester of tartaric acid containing more than one caffeic acid moieties, in any combination, and/or isomers thereof, and the corresponding salts.

Caffeic acid has the structure:

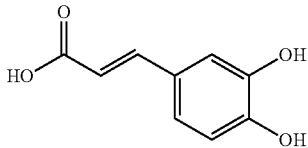 [SMILES: O=C(O)/C=C/c1ccc(O)c(O)c1]

Quinic acid has the structure:

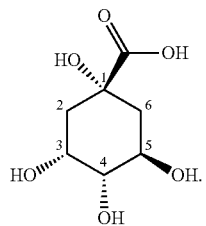 [SMILES: O=C(O)[C@]1(O)C[C@@H](O)[C@@H](O)[C@H](O)C1]

The structure provided above is D-(—)-quinic acid and the numbers shown correspond to current IUPAC numbering.

The various compounds described herein various stereochemical forms. For example, the described compounds can be racemic mixtures, enantiomerically pure compounds, and enantiomerically enriched mixtures, at any degree of enrichment. Individual optical isomers can be isolated or synthesized so as to be substantially free of their enantiomeric or diastereomeric partners, and these are all within the scope of the invention. In various embodiments, the compounds are used in their naturally-occurring stereochemical form. For example, the compounds can be in their botanically-occurring stereochemical form.

In some aspects, the stabilizer includes one or more of chlorogenic acid (5-O-caffeoylquinic acid), neochlorogenic acid (3-O-caffeoylquinic acid), cryptochlorogenic acid (4-O-caffeoylquinic acid), 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, rosmarinic acid, caftaric acid (monocaffeoyltartaric acid), cichoric acid (dicaffeoyltartaric acid) and salts, in any combination, and/or isomers thereof, and the corresponding salts.

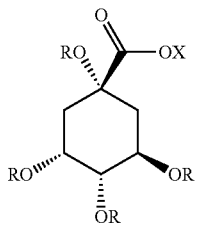

Formula I

In various aspects, the stabilizer includes one or more compounds according to Formula I and salts thereof. According to Formula I, R is H or an optionally substituted cinnamoyl group, X is H (acid form) or M (salt form), wherein M is a cationic metal such as sodium, potassium, or a mixture thereof, so as to result in a salt. Examples of optionally substituted cinnamoyl groups include, but are not limited to, caffeoyl, o-coumaroyl, p-coumaroyl, m-coumaroyl, cinnamoyl, 4-hydroxycinnamoyl, feruloyl, iso-feruloyl, or sinapoyl. In various embodiments, at least one R is an optionally substituted cinnamoyl group, at least two Rs are optionally substituted cinnamoyl groups, or exactly one R or two Rs are an optionally substituted cinnamoyl group. In various embodiments, at least one R is a caffeoyl group, at least two Rs are a caffeoyl group, or exactly one R or two Rs are a caffeoyl group.

The stabilizer can consist of one or more compounds selected from the list consisting of chlorogenic acid (5-O-caffeoylquinic acid), neochlorogenic acid (3-O-caffeoylquinic acid), cryptochlorogenic acid (4-O-caffeoylquinic acid), 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid, and any combination thereof, isomers thereof, and the corresponding salts. In various embodiments, one or more alcohol of the caffeoyl moiety is replaced with a hydrogen or substituted with an $C_1$-$C_{10}$ alkyl (e.g., methyl, ethyl, propyl, and the like), $C_1$-$C_{10}$ alkenyl, $C_6$-$C_{10}$ aryl, $C_2$-$C_{10}$ acyl, acrylate, caffeoyl, o-coumaroyl, p-coumaroyl, m-coumaroyl, cinnamoyl, 4-hydroxycinnamoyl, feruloyl, iso-feruloyl, sinapoyl, galloyl, sulfate, phosphate, or phosphonate. Thus, modified and substituted caffeic acid moieties result in a cinnamic acid, o-coumaroyl, p-coumaric acid, m-coumaric acid, ferulic acid, and the acyl and ester forms thereof. In various embodiments, one or more alcohol of the quinic acid moiety is substituted with an $C_1$-$C_{10}$ alkyl (e.g., methyl, ethyl, propyl, etc), $C_1$-$C_{10}$ alkenyl, $C_6$-$C_{10}$ aryl, $C_2$-$C_{10}$ acyl, acrylate, caffeoyl, o-coumaroyl, p-coumaroyl, m-coumaroyl, cinnamoyl, 4-hydroxycinnamoyl, feruloyl, iso-feruloyl, sinapoyl, galloyl, sulfate, phosphate, or phosphonate.

The stabilizer can include one or more of a caffeic ester of 3-(3,4-dihydroxyphenyl)lactic acid, a caffeic acid ester of tartaric acid, a ferulic ester of quinic acid or any other optionally-substituted cinnamoyl ester of quinic acid other than a caffeoylquinic acid. Examples of a ferulic ester of quinic acid includes 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, and combinations thereof. An example of a caffeic ester of 3-(3,4-dihydroxyphenyl)lactic acid is rosmarinic acid. Examples of a caffeic acid ester of tartaric acid includes cichoric acid, caftaric acid, monocaffeoyltartaric acid, dicaffeoyltartaric acid, and combinations thereof.

In an alternative embodiment, the stabilizer is a mixture consisting of one or more of a caffeic ester of 3-(3,4- dihydroxyphenyl)lactic acid, a caffeic acid ester of tartaric acid, a ferulic ester of quinic acid or any other optionally-substituted cinnamoyl ester of quinic acid other than a caffeoylquinic acid. Such stabilizer also includes salts thereof so as to have a salt fraction and an acid fraction. It is thus further envisaged that each of the various embodiments described herein related to caffeoylquinic acid and other stabilizers can be equally applicable to this alternative.

The stabilizer can include 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, salts thereof, or combinations thereof.

The stabilizer can include one or more monocaffeoylquinic acids, dicaffeoylquinic acids, salts thereof, or a combination thereof. The stabilizer can include a mixture of one or more monocaffeoylquinic acids, salts thereof, or a combination thereof; and one or more dicaffeoylquinic acids, salts thereof, or a combination thereof. The monocaffeoylquinic acid can be one or more of 3-O-caffeoylquinic acid, 4-O-caffeoylquinic acid, or 5-O-caffeoylquinic acid. The monocaffeoylquinic acid salt can be one or more of a salt of 3-O-caffeoylquinic acid, a salt of 4-O-caffeoylquinic acid, or a salt of 5-O-caffeoylquinic acid. The dicaffeoylquinic acid can be one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, or 4,5-dicaffeoylquinic acid. The dicaffeoylquinic acid salt can be one or more of a salt of 1,3-dicaffeoylquinic acid, a salt of 1,4-dicaffeoylquinic acid, a salt of 1,5-dicaffeoylquinic acid, a salt of 3,4-dicaffeoylquinic acid, a salt of 3,5-dicaffeoylquinic acid, or a salt of 4,5-dicaffeoylquinic acid. The salt of the monocaffeoylqunic acid or the salt of the dicaffeoylquinic acid can include a counterion that is sodium, potassium, calcium, magnesium, ammonium, or a combination thereof. The salt of the monocaffeoylqunic acid or the salt of the dicaffeoylquinic acid can include a counterion that is sodium, potassium, or a combination thereof.

The one or more SGMAs, salts thereof, or the combination thereof, can be any suitable proportion of the composition. The one or more SGMAs, salts thereof, or the combination thereof, can be 0.001 wt % to 99.999 wt % of the composition, 5 wt % to 99.999 wt %, 10 wt % to 99.999 wt %, 0.01 wt % to 90 wt %, 0.01 wt % to 30 wt %, or 0.001 wt % or more, or less than, equal to, or greater than 0.005 wt %, 0.01, 0.05, 0.1, 0.5, 1, 2, 3, 4, 5, 6, 8, 10, 12, 14, 16, 18, 20, 22, 24, 26, 28, 30, 32, 34, 36, 38, 40, 45, 50, 55, 60, 65, 70, 75, 80, 82, 84, 86, 88, 90, 92, 94, 95, 96, 97, 98, 99, 99.9, or 99.99 wt %, or 99.999 wt % or less of the composition. Compositions that are sweeteners can have a relatively high concentration of the one or more SGMAs, salts thereof, or combination thereof, such as 0.2 wt % to 99.999 wt %, or 5 wt % to 99.999 wt %. Compositions that are beverages such as carbonated soft drinks can have a comparatively lower concentration of the one or more SGMAs, salts thereof, or combination thereof, such as 0.01 wt % to 0.2 wt %, or 0.02 wt % to 0.1 wt %, or 0.03 wt % to 0.07 wt %.

The composition can have any suitable concentration of the one or more SGMAs, salts thereof, or combination thereof, such as 100 ppm to 500,000 ppm (i.e., parts per million by weight), 100 ppm to 2,000 ppm, 200 ppm to 1,000 ppm, 300 ppm to 700 ppm, or 100 ppm or more, or less than, equal to, or greater than 150 ppm, 200, 250, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,200, 2,400, 2,600, 2,800, 3,000, 3,500, 4,000, 5,000, 6,000, 8,000, 10,000, 20,000, 50,000, 100,000, 200,000, 300,000, or 400,000 ppm, or 500,000 ppm or less. Compositions that are sweeteners can have a relatively high concentration of the one or more SGMAs, salts thereof, or combination thereof, such as 100,000 ppm to 500,000 ppm or more. Compositions that are beverages such as carbonated soft drinks can have a comparatively lower concentration of the one or more SGMAs, salts thereof, or combination thereof, such as 100 ppm to 2,000 ppm, 200 to 1,000 ppm, or 300 ppm to 700 ppm.

The stabilizer can be any suitable proportion of the composition. The stabilizer can be 0.001 wt % to 99.999 wt % of the composition, 5 wt % to 99.999 wt %, 10 wt % to 99.999 wt %, 0.01 wt % to 90 wt %, 0.01 wt % to 30 wt %, or 0.001 wt % or more, or less than, equal to, or greater than 0.005 wt %, 0.01, 0.05, 0.1, 0.5, 1, 2, 3, 4, 5, 6, 8, 10, 12, 14, 16, 18, 20, 22, 24, 26, 28, 30, 32, 34, 36, 38, 40, 45, 50, 55, 60, 65, 70, 75, 80, 82, 84, 86, 88, 90, 92, 94, 95, 96, 97, 98, 99, 99.9, or 99.99 wt %, or 99.999 wt % or less of the composition. Compositions that are sweeteners can have a relatively high concentration of stabilizer, such as 0.2 wt % to 99.999 wt %, or 5 wt % to 99.999 wt %. Compositions that are beverages such as carbonated soft drinks can have a comparatively lower concentration of the stabilizer, such as 0.01 wt % to 0.2 wt %, or 0.02 wt % to 0.1 wt %, or 0.03 wt % to 0.07 wt %.

The composition can have any suitable concentration of the stabilizer. For example, the concentration of the stabilizer can be 100 ppm to 500,000 ppm (i.e., parts per million by weight), 100 ppm to 2,000 ppm, 200 ppm to 1,000 ppm, 300 ppm to 700 ppm, or 100 ppm or more, or less than, equal to, or greater than 150 ppm, 200, 250, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,200, 2,400, 2,600, 2,800, 3,000, 3,500, 4,000, 5,000, 6,000, 8,000, 10,000, 20,000, 50,000, 100,000, 200,000, 300,000, or 400,000 ppm, or 500,000 ppm or less. Compositions that are sweeteners can have a relatively high concentration of the stabilizer, such as 2,000 ppm to 500,000 ppm or more, e.g., 3,000 to 300,000 ppm, 4,000 ppm to 250,000 ppm, or 5,000 ppm to 200,000 ppm. Compositions that are beverages such as carbonated soft drinks can have a comparatively lower concentration of stabilizer, such as 100 ppm to 2,000 ppm, 200 to 1,000 ppm, or 300 ppm to 700 ppm.

The composition can have any suitable mass ratio of the one or more SGMAs, salts thereof, or combination thereof, to the stabilizer, such as 0.1:1 to 10:1, 1:5 to 3:1, 0.3:1 to 3:1, 0.5:1 to 2:1, or 0.1:1 or more, or less than, equal to, or greater than 0.2:1 (e.g., 1:5), 0.3:1, 0.4:1, 0.5:1, 0.6:1, 0.7:1, 0.8:1, 0.9:1, 1.0:1, 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.8:1, 4.0:1, 4.5:1, 5:1, 5.5:1, 6:1, 6.5:1, 7:1, 7.5:1, 8:1, 8.5:1, 9:1, 9.5:1, or 10:1 or less.

The composition can be substantially free (e.g., 0 wt %) of non-malonated steviol glycosides and salts thereof. The composition can include one or more non-malonated steviol glycosides, salts thereof, or a combination thereof. The non-malonated steviol glycosides or salts thereof can be any suitable non-malonated steviol glycosides or salts thereof, such as stevioside, rebaudioside A, rebaudioside C, dulcoside A, rebaudioside B, rebaudioside D, rebaudioside E, rebaudioside M, rebaudioside 0, rebaudioside N, rebaudioside F, salts thereof, or a combination thereof. The composition can have any suitable ratio (i.e., mass ratio) of non-malonated steviol glycosides, salts thereof, or a combination thereof to the one or more SGMAs, such as 0.001:1 to 1000:1, 0.1:1 to 1000:1, 2:1 to 1000:1, or 0.001:1 or more, or less than, equal to, or greater than 0.005:1, 0.01:1, 0.05:1, 0.1:1, 0.2:1, 0.3:1, 0.4:1, 0.5:1, 0.6:1, 0.7:1, 0.8:1, 0.9:1, 1.0:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 8:1, 10:1, 15:1, 20:1, 25:1, 50:1, 100:1, 150:1, 200:1, 250:1, 500:1, or 750:1, or 1000:1 or less. In some useful implementations, the composition has relatively little non-malonated steviol glycoside content, e.g., with a ratio of non-malonated steviol glycosides, salts thereof, or a combination thereof to the one or more SGMAs less than 0.3:1, e.g., 0 (i.e., no non-malonated steviol glycosides are present) to 0.3:1, 0 to 0.2:1, 0 to 0.1:1, 0 to 0.05:1, 0 to 0.01:1, 0 to 0.005:1, or 0 to 0.001:1.

The composition can be an aqueous composition. For example, 20 wt % or more, or at least 20 wt %, or the composition can be water. Any suitable amount of the composition can be water, such as 5 wt % or more, or less than, equal to, or greater than 6 wt %, 8, 10, 15, 20, 25, 30, 35, 40, 45, 50, 55, 60, 65, 70, 75, 80, 82, 84, 86, 88, 90, 92, 94, 96, 97, or 98 wt % or more.

The composition can have any suitable pH, such as a pH of 1 to 9, e.g., 1 to 7, 1.5 to 6, 1.7 to 4, 2.5 to 3.5 (e.g., a beverage such as a carbonated soft drink), 1.7 to 2.0 (e.g., a beverage concentrate such as a throw syrup), or both less than 9 and less than, equal to, or greater than 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.8, 4.0, 4.2, 4.4, 4.6, 4.8, 5, 5.5, 6, 6.5, 7, 7.5, 8, or 8.5.

The composition can have a solid form (e.g., is not a liquid composition), such as a powder or granulated solid. The composition can be a freeze-dried power. The composition can be a sweetener. The composition in a solid form can have any suitable water solubility. For example, the solid composition can have a water solubility of 80 wt % or more (i.e., the solid composition dissolved in deionized water at 22° C. to form an aqueous solution of which the solid composition is 80 wt % or more), or 1 wt % to 80 wt %, or 40 wt % to 80 wt %, or 0 wt %, or less than, equal to, or greater than 2 wt %, 4, 6, 8, 10, 15, 20, 25, 30, 35, 40, 45, 50, 55, 60, 65, 70, or 75 wt %, or 80 wt % or less.

The composition can be a solid food stuff, such as a snack bar, a dried fruit product, a cookie, a cereal, a chocolate, a chewing gum, a candy, a cake, a donut, or a combination thereof. The composition can be a pharmaceutical composition, a nutritional supplement, a dental composition, or a combination thereof.

The composition can be a sweetened beverage. The composition can be a chocolate milk, a tea, an energy drink, a drinkable yogurt, a flavored water, or a combination thereof. The composition can be a soft drink, i.e., a non-alcoholic, flavored beverage, such as a carbonated soft drink. The composition can be a beverage concentrate, such as a liquid water enhancer used to flavor or sweeten still water or a throw syrup that can be used to make a carbonated soft drink via addition of water and carbonation. The composition can be a sweetener, and can be a liquid, a solid, or a combination thereof.

The composition can include any suitable one or more additional components, or can be substantially free of one or more additional components. Examples of the one or more additional components include another stabilizer (e.g., another one or more materials, in addition to the stabilizer including one or more caffeoyl-substituted quinic acids or salts thereof, that stabilize the composition to acidic conditions), a microbial stabilizer (e.g., sodium benzoate or sodium sorbate), another sweetener, a bulking agent, erythritol, a desiccant, an anti-caking agent, or a combination thereof.

The composition can be substantially free of *stevia* plant matter that is not soluble in water or a water-miscible alcohol such as ethanol or methanol.

In various aspects, the composition can be stable under acidic conditions in the absence of steviol glycoside stabilizers that stabilize steviol glycosides to acidic conditions (e.g., prevent or significantly limit degradation). The degradation can include, for example, hydrolysis of the malonyl ester bond of the SGMA. Measuring change in total SGMA content can be a suitable measure of the amount of degradation that has occurred. The SGMAs, salts thereof, or the combination thereof can degrade more slowly over time under acidic conditions (e.g., at pH 1.7 to 4) as compared to a corresponding composition that includes less or none of the stabilizer. For example, SGMAs in the composition can be stable (e.g., less than 20 wt %, 10 wt %, 5 wt %, 1 wt %, or less than 0.1 wt % degradation of the SGMA or salt thereof at 22° C. over 4 weeks, 2 months, 4 months, 6 months, 1 year, 2 years, or 3 years or more) at a pH of 1 to 9, 1.7 to 4, 2.5 to 3.5, 1.7 to 2.0, 4 to 9, or 1 or more, or less than, equal to, or greater than 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.8, 4.0, 4.2, 4.4, 4.6, 4.8, 5, 5.5, 6, 6.5, 7, 7.5, 8, 8.5, or 9 or less.

In one suitable standardized test for measuring degradation of the SGMAs in a composition, the composition is dissolved in an aqueous, alcohol-free buffered citric acid solution having a SGMA concentration of 50,000 ppm (5 wt %) and a pH of 1.7, which is stored at 22° C. This degradation test can be used to measure degradation over a fixed period of time. For example, compositions of the invention can have an SGMA content after 7 days that is equal to or greater than 85 wt %, 90%, 92%, 94%, 95%, 96%, or 97%, or 98% or more of the SGMA content present at the outset of the test. This degradation test can also be used to measure how long it takes to reach a fixed amount of degradation. For example, compositions of the invention can have an SGMA content that is at least 90 wt % of the SGMA content present at the outset of the test after storage for at least 4 days, at least 5 days, at least 7 days, at least 10 days, at least 14 days, or at least 20 days. The composition having a pH of 1.7 over 5 days at 22° C. can be stable such that 90 wt % of more of the SGMAs, salts thereof, or the combination thereof are undegraded. The composition having a pH of 1.7 over 35 days at 22° C. can be stable such that 50% or more of the SGMAs, salts thereof, or the combination thereof are undegraded.

The composition can be substantially free of materials from *stevia* leaf that are removed during a chromatographic separation to obtain the SGMA or salts thereof of the composition. For example, the composition can be substantially free of organic acid, citric acid, malic acid, phosphate, sulfate, colored bodies, chlorophyll, flavonoids, rutin, quercetin, quercitrin, glucose, fructose, amino acids, proteins, MCQAs, DCQAs, or a combination thereof.

Some compounds can adversely impact the flavor or aroma of the composition. In various aspects, the composition does not include one or more of the compounds shown in Table 1, or any combination thereof, above the disclosed preferred content levels. All preferred content levels are stated as weight percentage on a dry weight basis. For those compounds listed that are acids, the compound may be present in acid form and/or in salt form.

TABLE 1

| Class of compounds | Preferred Content Level (% wt) | % wt of compounds in solid (dry) compositions |
|---|---|---|
| Organic acids | <3%, preferably <2%, <1%, or 0% | malonate, malonic acid, oxalate, oxalic acid, lactate, lactic acid, succinate, succinic acid, malate, malic acid, citrate, citric acid |
| | <0.5%, preferably <0.25% or 0% | tartrate, tartaric acid, pyruvate, pyruvic acid, fumarate, fumaric acid, ascorbic acid, sorbate, sorbic acid, acetate, acetic acid |
| Inorganic acids | <1%, preferably <0.5% or 0% | sulfate, sulfuric acid, phosphate, phosphoric acid, nitrate, nitric acid, nitrite, nitrous acid, chloride, hydrochloric acid, ammonia, ammonium |
| Flavanoids, isoflavanoids, and neoflavanoids | <5%, preferably <4%, <3%, or <2%, more preferably <1%, <0.5%, or 0% | quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein |
| Flavanoid glycosides | <5%, preferably <4%, <3%, or <2%, more preferably <1%, <0.5%, or 0% | hesperidin, naringin, rutin, quercitrin, luteolin-glucoside, quercetin-xyloside |
| Anthocyanidins | <5%, preferably <4%, <3%, or <2%, more preferably <1%, <0.5%, or 0% | cyanidin, delphinidin, malvidin, pelargonidin, peonidin, petunidin |
| Tannins | <1%, preferably <0.5%, <0.25%, or 0% | tannic acid |
| Amino acids + total protein | <0.1%, preferably <0.05%, or 0% | alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1%, preferably <0.5%, <0.25%, or 0% | monoglycerides, diglycerides, triglycerides |
| Monosaccharides, disaccharides, and polysaccharides | <1% | glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose |
| Sugar alcohols | <1% | glycerol, sorbitol, mannitol, xylitol, maltitol, lactitol, erythritol, isomalt, inositol |
| Dietary fiber | <0.1%, preferably <0.05% or 0% | acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, psyllium husk mucilage, resistant starches, tara gum, tragacanth gum, xanthan gum, cellulose, chitin, and chitosan |
| Steviol glycoside compounds | <55% | stevioside; steviolbioside; rubusoside; 13- and 19-SMG; dulcosides A, B, C, D; and rebaudiosides A, B, C, D, E, F, I, M, N, O, T |
| Saponins | <2%, preferably <1%, <0.5%, <0.25%, or 0% | glycosylated ursolic acid and glycosylated oleanolic acid |
| Terpenes other than saponins and steviol glycoside compounds | <2%, preferably <1%, <0.5%, <0.25%, or 0% | eugenol, geraniol, geranial, alpha-ionone, beta-ionone, epoxy-ionone, limonene, linalool, linalool oxide, nerol, damascenone |
| Lipid oxidation products | <2%, preferably <1%, <0.5%, <0.25%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.1%, preferably <0.05% or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |

TABLE 1-continued

| Class of compounds | Preferred Content Level (% wt) | % wt of compounds in solid (dry) compositions |
|---|---|---|
| Other compounds | <0.1%, preferably <0.05% or 0% | chlorophyll, furans, furan-containing chemicals, theobromine, theophylline, and trigonelline |
| | <1%, preferably <0.5%, <0.25%, or 0% | saponins |

In one aspect, the composition in a solid (dry) form does not include one or more of the following compounds in Table 2, or any combination thereof, above the disclosed preferred content levels. All preferred content levels are stated as weight percentage on a dry weight basis. For those compounds listed that are acids, the compound may be present in acid form and/or in salt form.

TABLE 2

| Class of compounds | Preferred Content Level (% wt) | % wt of compounds in solid (dry) composition |
|---|---|---|
| Organic acids | <3%, preferably <2%, <1%, or 0% | Malonate, malonic acid, Oxalate, oxalic acid, Lactate, lactic acid, Succinate, succinic acid, Malate, malic acid, Citrate, citric acid |
| | <0.5%, preferably <0.25% or 0% | Tartrate, tartaric acid, Pyruvate, pyruvic acid, Fumarate, fumaric acid, Ascorbic acid, Sorbate, sorbic acid, Acetate, acetic acid |
| Inorganic acids | <1%, preferably <0.5% or 0% | Sulfate, sulfuric acid, Phosphate, phosphoric acid, Nitrate, nitric acid, Nitrite, nitrous acid, Chloride, hydrochloric acid, Ammonia, ammonium |
| Flavanoids, isoflavanoids, and neoflavanoids | <5%, preferably <4%, <3%, or <2%, more preferably <1%, <0.5%, or 0% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <5%, preferably <4%, <3%, or <2%, more preferably <1%, <0.5%, or 0% | Hesperidin, Naringin, Rutin, Quercitrin, luteolin-glucoside, quercetin-xyloside |
| Anthocyanidins | <5%, preferably <4%, <3%, or <2%, more preferably <1%, <0.5%, or 0% | Cyanidin, Delphinidin, Malvidin, Pelargonidin, Peonidin, Petunidin |
| Tannins | <1%, preferably <0.5%, <0.25%, or 0% | Tannic acid |
| Amino acids + total protein | <0.1%, preferably <0.05%, or 0% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1%, preferably <0.5%, <0.25%, or 0% | Monoglycerides, diglycerides, triglycerides |
| Monosaccharides, disaccharides, and polysaccharides | <1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <1% | Glycerol, Sorbitol, mannitol, xylitol, maltitol, lactitol, erythritol, isomalt, inositol |
| Dietary fiber | <0.1%, preferably <0.05% or 0% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Poly dextrose, Psyllium husk mucilage, Resistant starches, Tara gum, Tragacanth gum, Xanthan gum, Cellulose, Chitin, and Chitosan |

TABLE 2-continued

| Class of compounds | Preferred Content Level (% wt) | % wt of compounds in solid (dry) composition |
|---|---|---|
| Steviol glycoside compounds | <75% | Stevioside; steviolbioside; rubusoside; 13- and 19-SMG; Dulcosides A, B, C, D; and rebaudiosides A, B, C, D, E, F, I, M, N, O, T |
| Saponins | <1%, preferably <0.5%, <0.25%, or 0% | glycosylated ursolic acid and glycosylated oleanolic acid |
| Terpenes other than saponins and steviol glycoside compounds | <1%, preferably <0.5%, <0.25%, or 0% | eugenol, geraniol, geranial, alpha-ionone, beta-ionone, epoxy-ionone, limonene, linalool, linalool oxide, nerol, damascenone |
| Lipid oxidation products | <1%, preferably <0.5%, <0.25%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.05%, preferably <0.01% or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.1%, preferably <0.05% or 0% | chlorophyll, furans, furan-containing chemicals, theobromine, theophylline, and trigonelline |

In one aspect, the composition does not include one or more of the following compounds in Table 3, or any combination thereof, above the disclosed preferred content levels. These preferred content levels are stated as weight percentage of a liquid composition (e.g., a liquid sweetener concentrate, such as a throw syrup). For those compounds listed that are acids, the compound may be present in acid form and/or in salt form, taking into account either may be dissociated in the composition.

TABLE 3

| Class of compounds | Preferred Content Level (% wt) | % (wt) of compounds in liquid compositions |
|---|---|---|
| Organic acids | <0.3%, preferably <0.2%, <0.1%, or 0% <0.05%, preferably <0.025% or 0% | Malonate, malonic acid, Oxalate, oxalic acid, Lactate, lactic acid, Succinate, succinic acid, Malate, malic acid Tartrate, tartaric acid, Pyruvate, pyruvic acid, Fumarate, fumaric acid, Ascorbic acid, Sorbate, sorbic acid, Acetate, acetic acid |
| Inorganic acids | <1%, preferably <0.05% or 0% | Sulfate, sulfuric acid, Nitrate, nitric acid, Nitrite, nitrous acid, Chloride, hydrochloric acid, Ammonia, ammonium |
| Flavanoids, isoflavanoids, and neoflavanoids | <0.5%, preferably <0.4%, <0.3%, or <0.2%, more preferably <0.1%, <0.05%, or 0% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <0.5%, preferably <0.4%, <0.3%, or <0.2%, more preferably <0.1%, <0.05%, or 0% | Hesperidin, Naringin, Rutin, Quercitrin, luteolin-glucoside, quercetin-xyloside |
| Anthocyanidins | <0.5%, preferably <0.4%, <0.3%, or <0.2%, more preferably <0.1%, <0.05%, or 0% | Cyanidin, Delphinidin, Malvidin, Pelargonidin, Peonidin, Petunidin |
| Tannins | <0.1%, preferably <0.05%, <0.025%, or 0% | Tannic acid |

TABLE 3-continued

| Class of compounds | Preferred Content Level (% wt) | % (wt) of compounds in liquid compositions |
|---|---|---|
| Amino acids + total protein | <0.01% preferably <0.005%, or 0% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <0.1%, preferably <0.05%, <0.025%, or 0% | Monoglycerides, diglycerides, triglycerides |
| Monosaccharides, disaccharides, and polysaccharides | <0.1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <0.1% | Glycerol, Sorbitol, mannitol, xylitol, maltitol, lactitol, erythritol, isomalt, inositol |
| Dietary fiber | <0.01%, preferably <0.005% or 0% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Poly dextrose, Psyllium husk mucilage, Resistant starches, Tara gum, Tragacanth gum, Xanthan gum, Cellulose, Chitin, and Chitosan |
| Saponins | <0.5%, preferably <0.4%, <0.3%, or <0.2%, more preferably <0.1%, <0.05%, or 0% | glycosylated ursolic acid and glycosylated oleanolic acid |
| Terpenes other than steviol glycoside compounds and saponins | <0.5%, preferably <0.4%, <0.3%, or <0.2%, more preferably <0.1%, <0.05%, or 0% | eugenol, geraniol, geranial, alpha-ionone, beta-ionone, epoxy-ionone, limonene, linalool, linalool oxide, nerol, damascenone |
| Lipid oxidation products | <0.5%, preferably <0.4%, <0.3%, or <0.2%, more preferably <0.1%, <0.05%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.01 (100 ppm), preferably <0.005% (50 ppm), or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.05%, preferably <0.01% or 0% | chlorophyll, furans, furan-containing chemicals, theobromine, theophylline, and trigonelline |

In one aspect, the composition is a liquid sweetener concentrate or a beverage and does not include one or more of the following compounds listed in Table 4, or any combination thereof, at the disclosed wt % cutoffs. All preferred content levels are stated as weight percentage of the total liquid sweetener concentrate or the beverage. For those compounds listed that are acids, the compound may be present in acid form and/or in salt form, taking into account that either may be dissociated in the beverage.

TABLE 4

| Class of compounds | Preferred Content Level (% wt) | % (wt) of compounds in compositions that are beverages |
|---|---|---|
| Organic acids | <0.1%, preferably <0.05%, <0.025%, or 0% | Malonate, malonic acid, Oxalate, oxalic acid, Pyruvate, pyruvic acid, Fumarate, fumaric acid |
| Inorganic acids | <1%, preferably <0.05% or 0% | Sulfate, sulfuric acid, Nitrate, nitric acid, Nitrite, nitrous acid, Ammonia, ammonium |

TABLE 4-continued

| Class of compounds | Preferred Content Level (% wt) | % (wt) of compounds in compositions that are beverages |
| --- | --- | --- |
| Flavanoids, isoflavanoids, and neoflavanoids | <0.5%, preferably <0.4%, <0.3%, or <0.2%, more preferably <0.1%, <0.05%, or 0% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <0.5%, preferably <0.4%, <0.3%, or <0.2%, more preferably <0.1%, <0.05%, or 0% | Hesperidin, Naringin, Rutin, Quercitrin, luteolin-glucoside, quercetin-xyloside |
| Anthocyanidins | <0.5%, preferably <0.4%, <0.3%, or <0.2%, more preferably <0.1%, <0.05%, or 0% | Cyanidin, Delphinidin, Malvidin, Pelargonidin, Peonidin, Petunidin |
| Tannins | <0.1%, preferably <0.05%, <0.025%, or 0% | Tannic acid |
| Amino acids + total protein | <5%, preferably <1%, <0.5%, <0.1% <0.05%, or 0% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <0.5%, preferably <0.1%, <0.05%, <0.025%, or 0% | Monoglycerides, diglycerides, triglycerides |
| Dietary fiber | <5%, preferably <1%, <0.5%, <0.1% <0.05%, or 0% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Saponins | <0.1%, preferably <0.05%, <0.025%, or 0% | glycosylated ursolic acid and glycosylated oleanolic acid |
| Terpenes other than saponins and steviol glycoside compounds | <0.1%, preferably <0.05%, <0.025%, or 0% | eugenol, geraniol, geranial, alpha-ionone, beta-ionone, epoxy-ionone, limonene, linalool, linalool oxide, nerol, damascenone |
| Lipid oxidation products | <0.1%, preferably <0.05%, <0.025%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.001% (10 ppm), preferably <0.0005% (5 ppm), or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.05%, preferably <0.01% or 0% | chlorophyll, furans, furan-containing chemicals, theobromine, theophylline, and trigonelline |

Steviol Glycoside Malonic Acid Ester.

The compositions of the present invention include a steviol glycoside malonic acid ester (SGMA) or salt thereof. The SGMA includes one or more malonic acid ester groups, such as 1-3 malonic acid ester groups or more (e.g., no more than 1-3 malonic acid ester groups), 2 malonic acid ester groups (e.g., no more than 2 malonic acid ester groups), or 1 malonic acid ester group (e.g., no more than 1 malonic acid ester group). The malonic acid ester group can have the structure:

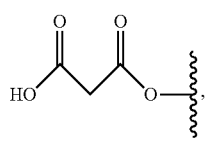

or a salt thereof.

The SGMA salt can be any suitable salt of the SGMA. For example, the salt can be a malonic acid salt including a counterion that is sodium, potassium, calcium, magnesium, ammonium, or a combination thereof. The salt can be a malonic acid salt including a counterion that is sodium, potassium, or a combination thereof.

The SGMA can be any suitable steviol glycoside including a malonic acid ester group. The SGMA can include one or more of glucose, xylose, rhamnose, or a combination thereof. The SGMA can have the structure:

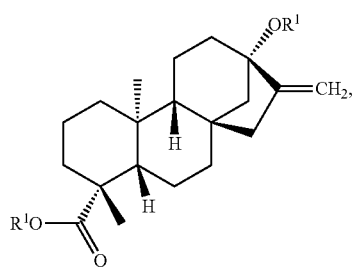

or a salt thereof. At each occurrence $R^1$ can be independently chosen from —H, a malonic acid ester or a salt thereof, and a glycosidically-bonded primary sugar. At each occurrence the primary sugar can be independently chosen from glucose, xylose, and rhamnose, and at each occurrence the primary sugar can independently optionally include a secondary sugar glycosidically-bonded to the primary sugar, a malonic acid ester or a salt thereof bonded to the primary sugar, or a combination thereof. At each occurrence the secondary sugar, if present, can be independently chosen from glucose, xylose, and rhamnose, and at each occurrence the secondary sugar can independently optionally include a tertiary sugar glycosidically-bonded to the secondary sugar, a malonic acid ester or a salt thereof bonded to the secondary sugar, or a combination thereof. At each occurrence the tertiary sugar, if present, can be independently chosen from glucose, xylose, and rhamnose, and at each occurrence the tertiary sugar can independently optionally include a malonic acid ester or a salt thereof bonded to the tertiary sugar. The SGMA includes at least one of the primary sugars and at least one of the malonic acid ester groups or a salt thereof.

The SGMA can be free of the secondary sugars. The SGMA can include at least one of the secondary sugars. The SGMA can be free of the tertiary sugars. The SGMA can include at least one of the tertiary sugars.

The SGMA can have the structure:

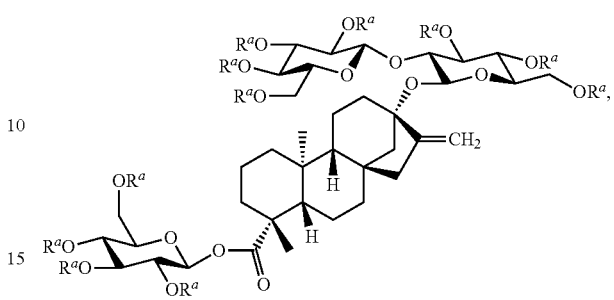

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

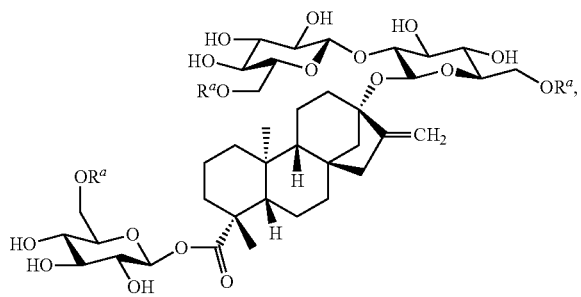

or a salt thereof. The SGMA can have the structure:

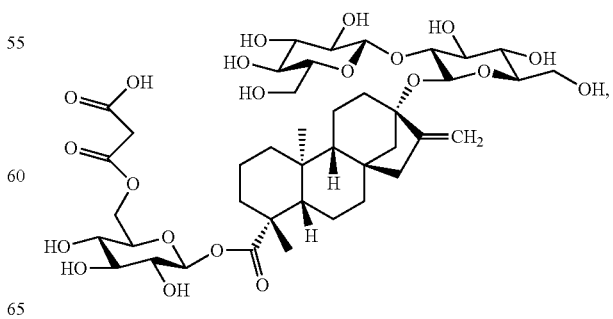

or a salt thereof.

The SGMA can have the structure:

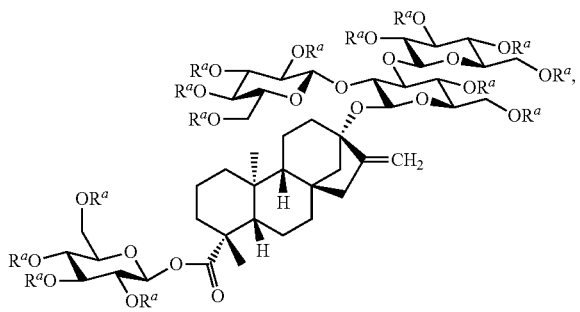

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

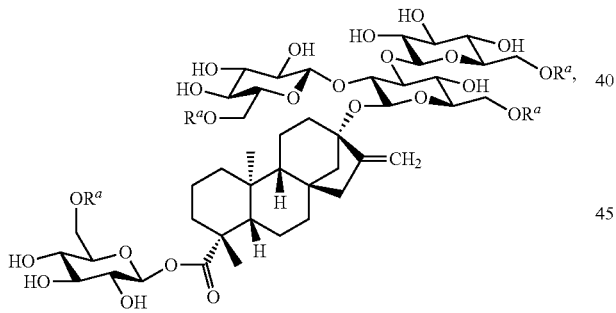

or a salt thereof. The SGMA can have the structure:

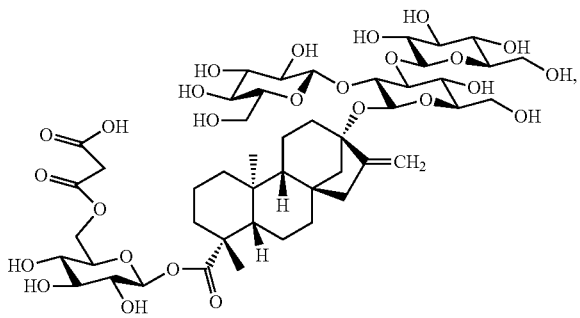

or a salt thereof. The SGMA can have the structure:

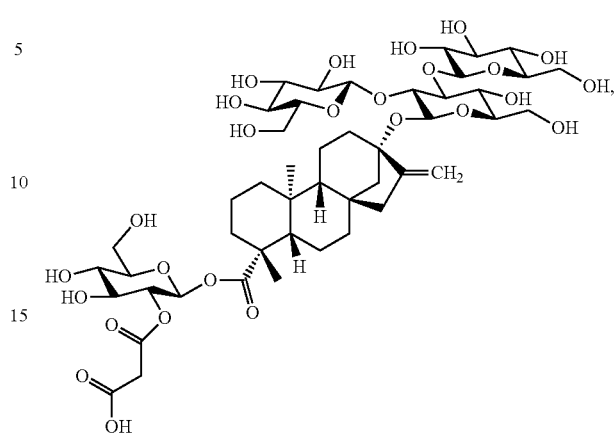

or a salt thereof.

The SGMA can have the structure:

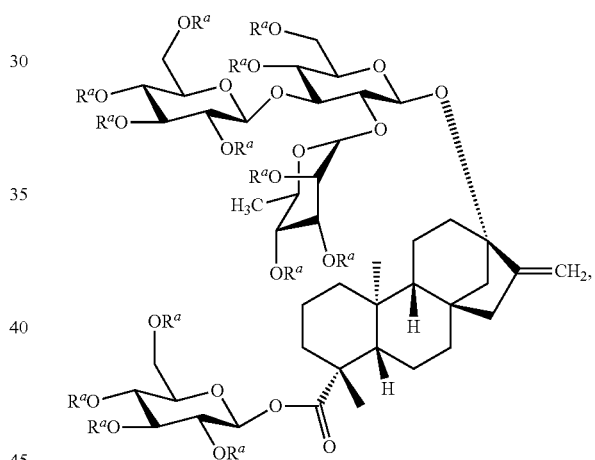

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

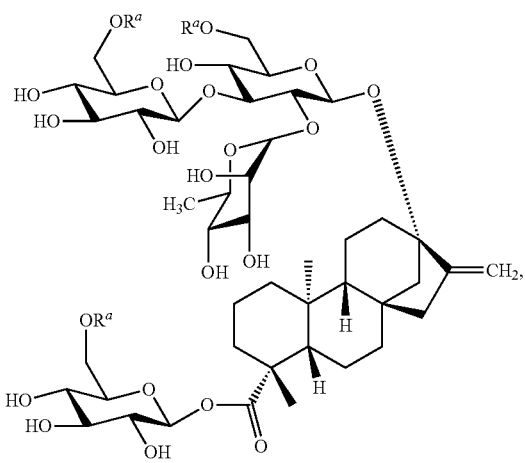

or a salt thereof. The SGMA can have the structure:

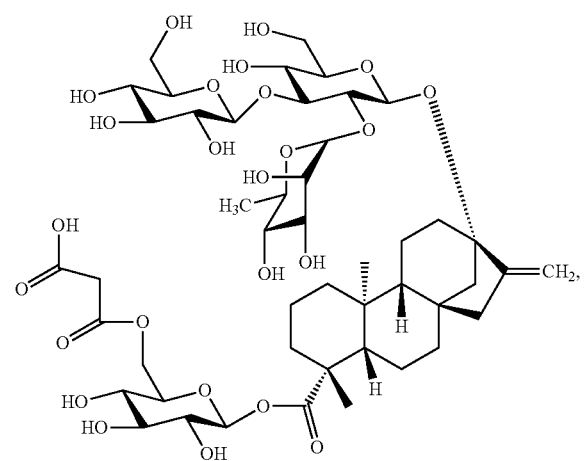

or a salt thereof.
The SGMA can have the structure:

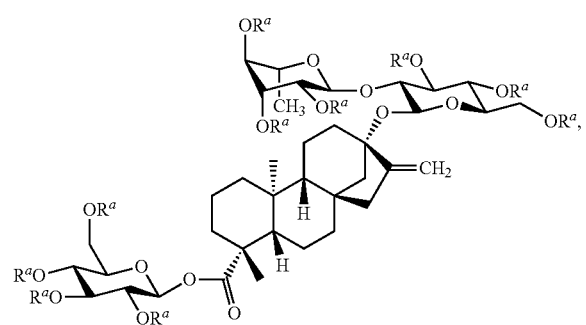

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

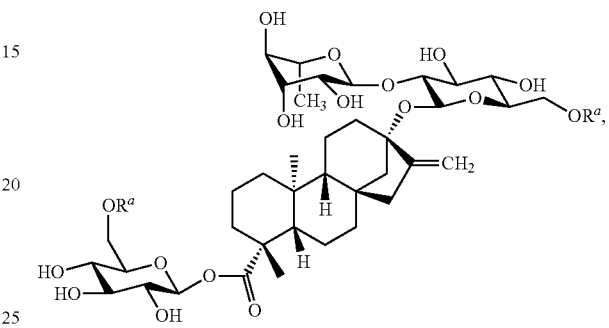

or a salt thereof.
The SGMA can have the structure:

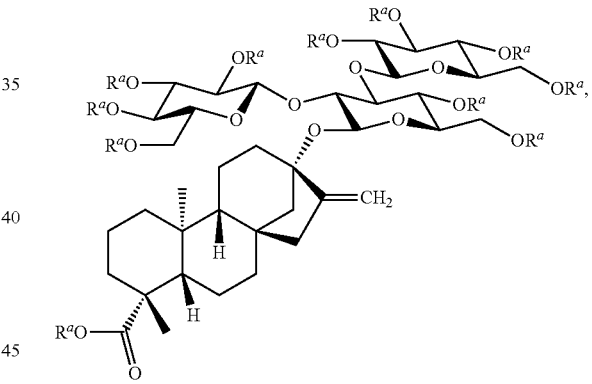

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

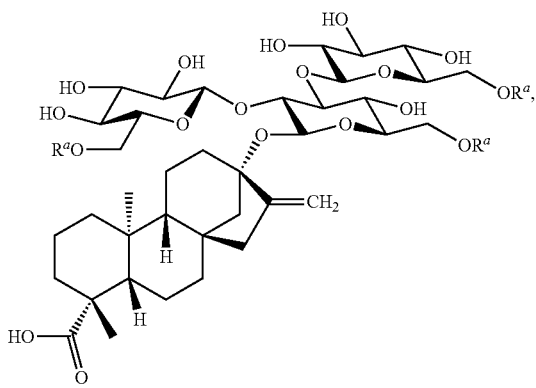

or a salt thereof.
The SGMA can have the structure:

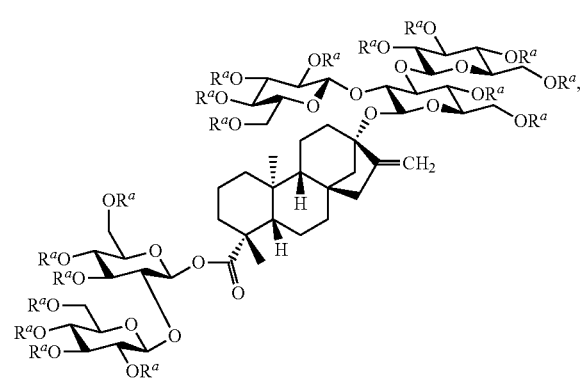

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

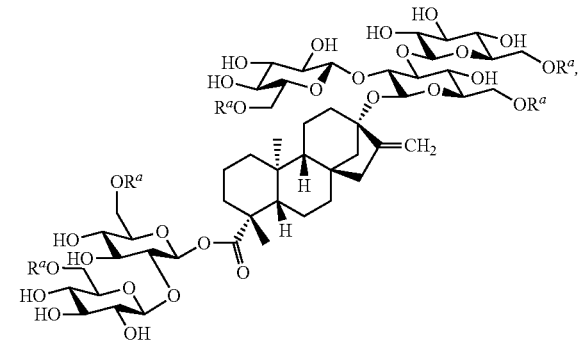

or a salt thereof.
The SGMA can have the structure:

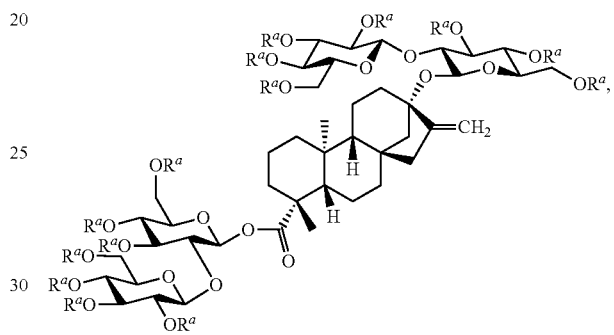

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

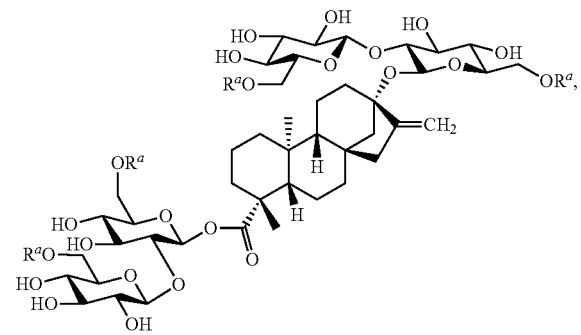

or a salt thereof.

The SGMA can have the structure:

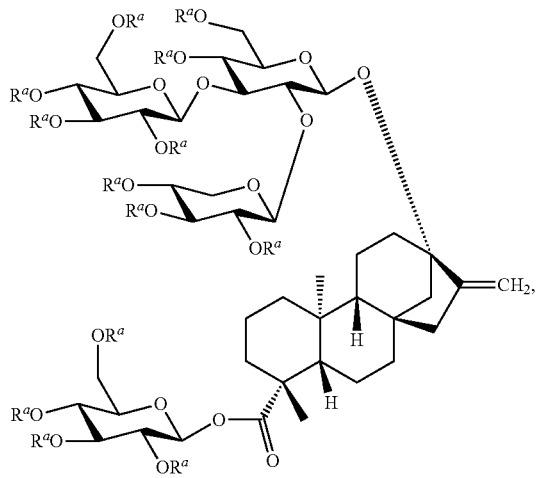

or a salt thereof. At each occurrence $R^a$ can be independently chosen from —H, a malonic acid ester or a salt thereof, and a sugar. At each occurrence the sugar can be independently chosen from glucose, xylose, and rhamnose. At each occurrence the sugar can independently optionally include a malonic acid ester or a salt thereof bonded to the sugar. For example, each of the sugars can independently be free of a malonic acid ester or a salt thereof bonded thereto, or can include a malonic acid ester or a salt thereof bonded thereto. The SGMA includes at least one malonic acid ester or a salt thereof (e.g., one or more $R^a$ is a malonic acid ester or a salt thereof, one or more sugars include a malonic acid ester or a salt thereof bonded thereto, or a combination thereof).

At each occurrence $R^a$ can be independently chosen from —H and a malonic acid ester or a salt thereof, wherein at least one $R^a$ is a malonic acid ester or a salt thereof. The SGMA can have the structure:

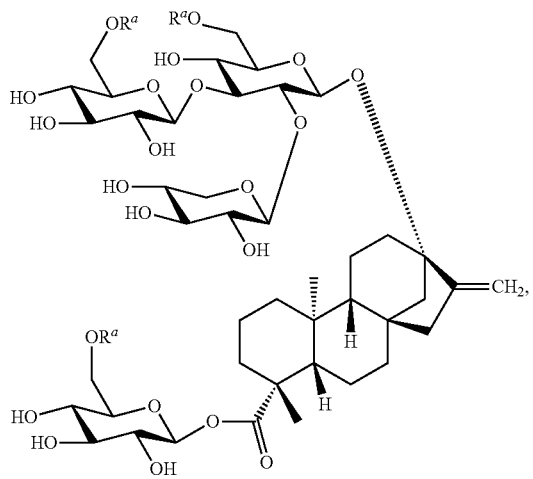

or a salt thereof. The SGMA can have the structure:

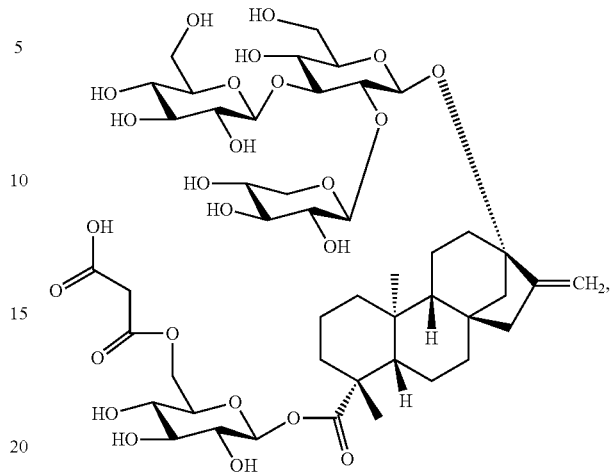

or a salt thereof.

The SGMA can have any suitable water solubility. For example, the SGMA can have a water solubility 40 wt % or more (i.e., the SGMA is dissolved in deionized water at 22° C. to form an aqueous solution that is 40 wt % or more SGMA), or 0 wt % to 40 wt %, or 20 wt % to 40 wt %, or 0 wt %, or 1 wt % or less, or less than, equal to, or greater than 2 wt %, 4, 6, 8, 10, 15, 20, 25, 30, 35, or 40 wt % or more.

Method of Making Composition Including SGMAs and Stabilizer

Various aspects of the present invention provide a method of making the composition including the one or more SGMAs or salts thereof and the stabilizer. The method can be any suitable method that forms the composition. The method can include combining the one or more SGMAs, salts thereof, or combination thereof and the stabilizer to form the composition.

Various aspects of the present invention provide a method of making a composition including one or more steviol glycoside malonic acid esters (SGMAs) or salts thereof and a stabilizer including one or more caffeoyl-substituted quinic acids or salts thereof. The method can include combining a SGMA component that includes the one or more SGMAs, salts thereof, or combination thereof with a stabilizer component that includes the stabilizer to form the composition including one or more steviol glycoside malonic acid esters (SGMAs) or salts thereof and a stabilizer including one or more caffeoyl-substituted quinic acids or salts thereof.

SGMAs, salts thereof, or a combination thereof may be any suitable proportion of the SGMA component. Preferably, though, at least 30 weight percent on a dry-weight basis (wt % dwb) of the SGMA component is SGMAs, salts thereof, or the combination thereof. For example, the SGMAs, salts thereof, or the combination thereof may be 30 wt % dwb to 99.9 wt % dwb, 40 wt % dwb to 99.9 wt % dwb, 50 wt % to 99.9 wt % dwb, 80 wt % to 99.9 wt % dwb, 90 wt % to 99.9 wt % dwb, or both at least 5 wt % dwb and less than, equal to, or greater than 6 wt % dwb, 7, 8, 10, 12, 14, 16, 18, 20, 22, 24, 26, 28, 30, 32, 34, 36, 38, 40, 45, 50, 55, 60, 65, 70, 75, 80, 82, 84, 86, 88, 90, 92, 94, 95, 96, 97, 98, 99, 99.9, or 99.99 wt % dwb of the SGMA component. In use, the SGMA component may be in dry, solid form or in a solution, e.g., a nonalcoholic aqueous solution.

The stabilizer component can include any suitable proportion, preferably at least 30 wt % dwb (e.g., 30 wt % dwb to 99.9 wt % dwb, 40 wt % dwb to 99.9 wt % dwb, 50 wt % to 99.9 wt % dwb, 80 wt % to 99.9 wt % dwb, 90 wt % to 99.9 wt % dwb) of the following acids and esters: quinic acid, caffeic acid, ferulic acid, sinapic acid, p-coumaric acid, an ester of quinic acid, an ester of caffeic acid, an ester of ferulic acid, an ester of sinapic acid, an ester of p-coumaric acid, an ester of caffeic acid and quinic acid, an ester of caffeic acid and quinic acid including a single caffeic acid moiety, an ester of caffeic acid and quinic acid including more than one caffeic acid moiety, an ester of ferulic acid and quinic acid, an ester of ferulic acid and quinic acid including a single ferulic acid moiety, an ester of ferulic acid and quinic acid including more than one ferulic acid moiety, an ester of sinapic acid and quinic acid, an ester of sinapic acid and quinic acid including a single sinapic acid moiety, an ester of sinapic acid and quinic acid including more than one sinapic acid moiety, an ester of p-coumaric acid and quinic acid, an ester of p-coumaric acid and quinic acid including a single p-coumaric acid moiety, an ester of p-coumaric acid and quinic acid including more than one p-coumaric acid moiety, a di-ester of quinic acid containing one caffeic acid moiety and one ferulic acid moiety, a caffeic ester of 3-(3,4-dihydroxyphenyl)lactic acid, a caffeic ester of tartaric acid, a caffeic acid ester of tartaric acid containing more than one caffeic acid moieties, in any combination, and/or isomers thereof, and the corresponding salts. The stabilizer can include one or more caffeoyl-substituted quinic acids or salts thereof. Preferably, though, at least 30 wt % dwb of the stabilizer component is the one or more caffeoyl-substituted quinic acids or salts thereof, such as one or more monocaffeoylquinic acids, dicaffeoylquinic acids, salts thereof, or a combination thereof. For example, the one or more caffeoyl-substituted quinic acids or salts thereof may be 30 wt % dwb to 99.9 wt % dwb, 40 wt % dwb to 99.9 wt % dwb, 50 wt % to 99.9 wt % dwb, 80 wt % to 99.9 wt % dwb, 90 wt % to 99.9 wt % dwb, or at least 5 wt % dwb and less than, equal to, or greater than 6 wt % dwb, 7, 8, 10, 12, 14, 16, 18, 20, 22, 24, 26, 28, 30, 32, 34, 36, 38, 40, 45, 50, 55, 60, 65, 70, 75, 80, 82, 84, 86, 88, 90, 92, 94, 95, 96, 97, 98, 99, 99.9, or 99.99 wt % dwb of the stabilizer component. In use, the stabilizer component can be in dry, solid form or in a solution, e.g., a nonalcoholic aqueous solution.

Various aspects of the present invention provide a method of making a composition, such as a sweetener or sweetened composition. The sweetened composition can be a beverage concentrate (e.g., a throw syrup, a water enhancer, or a flavored water enhancer), a sweetened beverage (e.g., tea or a carbonated soft drink), a solid food stuff, a pharmaceutical composition, a nutritional supplement, or a dental composition. The method can include combining the SGMA component that includes one or more SGMAs with the stabilizer component that includes one or more stabilizers to form the composition. For forming beverages and beverage concentrates, the SGMA component and the stabilizer component can be combined before adding to the beverage or concentrate, can be added to the beverage or concentrate separately, or can be added separately to another composition that is added to the beverage or concentrate. In various aspects, the composition is a beverage or beverage concentrate, and the method further includes combining the SGMA component and the stabilizer component in an aqueous solution having a pH of 1 to 6. The SGMA component and the stabilizer component can be combined before they are added to the aqueous solution, the SGMA component and stabilizer component can be added separately to the aqueous solution, or can be added separately to another composition that is added to the beverage.

Either, and preferably both, of the SGMA component and the stabilizer component may include 0-5% (wt) of one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin; or 0-3% (wt) is one or more of malonate, malonic acid, oxalate, oxalic acid, lactate, lactic acid, succinate, succinic acid, malate, malic acid, citrate, and citric acid; or 0-1% (wt) is one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol; or 0-0.5% (wt) is one or more of tartrate, tartaric acid, pyruvate, pyruvic acid, fumarate, fumaric acid, ascorbic acid, sorbate, sorbic acid, acetate, acetic acid, and chlorophyll; or a combination thereof.

Either, and preferably both, of the SGMA component and the stabilizer component can be free of or have limited content of compounds that can adversely impact flavor or aroma. For example, either or both of the SGMA component and the stabilizer component the precursor does not include one or more of the compounds shown in Tables 1-4, or any combination thereof, above the disclosed preferred content levels. The SGMA component can be similar or identical to embodiments of the composition including one or more SGMAs of salts thereof described herein but lacking the stabilizer component added in the method.

EXAMPLES

Various embodiments of the present invention can be better understood by reference to the following Examples which are offered by way of illustration. The present invention is not limited to the Examples given herein.

Example 1. Malonated Steviol Glycoside Acid Stabilization

SGMA was obtained from *stevia* leaf as follows. Powdered dry *stevia* leaf (160 g) was extracted with 50% vol/vol ethanol in water (1600 mL) for 60 min with occasional stirring. The solid plant matter was removed via filtration through a Buchner funnel and Whatman 54 filter paper. The residual plant mass was washed with an additional volume of 50% vol/vol ethanol in water (800 mL). The initial extract was treated with ethyl acetate (1:1 extraction volume) to remove hydrophobic colored bodies and any residual ethyl acetate was allowed to evaporate under a stream of nitrogen. The clarified extract was then passed through an anionic resin (Dowex 66) to bind the ionic SGMA species. The resin was washed with aqueous ethanol (50%) to remove all neutral species, including traditional SGs. The SGMAs were then eluted with aqueous ethanol (50%) containing 5% sodium acetate. The eluent was collected and dried to remove excess ethanol. Once<10% ethanol remained, the eluent was acidified with HCl to pH 1-2 and was desalted on a hydrophobic resin (Diaion Sepabeads SP70) by loading directly, followed by washing with 15% vol/vol ethanol and eluting with 70% ethanol. The desalted eluent was then dried under nitrogen to remove the ethanol and lyophilized to complete dryness.

Aspartame was used to benchmark degradation of the steviol glycoside malonic acid esters (SGMAs). Aspartame has demonstrated commercially acceptable shelf life in a wide variety of common retail food and beverage products, including many carbonated soft drinks that have a pH below 4. Initial testing demonstrated that SGMA stability was worse than aspartame at pH 1.7 and 3.0 without the stabilizer.

The stabilizer was formed by extracting and purifying monocaffeoylquinic acids (MCQAs) and dicaffeoylquinic acids (DCQAs) from yerba mate leaf. Yerba mate leaf (300 g) was added to a glass container and a solution of 50% vol/vol ethanol in water (1500 mL) was also added and allowed to extract for 60 minutes with occasional stirring. The solution was filtered through a Buchner funnel and Whatman 54 filter paper. The residual plant mass was washed with additional water to increase yields and to obtain an extract containing 35% ethanol (vol/vol). This extract was loaded onto an ion exchange resin (Amberlite FPA53) and the resin was washed with 35% ethanol (vol/vol). The MCQAs and DCQAs were eluted with a solution of 50% ethanol (vol/vol) containing 10% (wt/vol) sodium chloride. The ethanol was evaporated from this eluent and the pH was adjusted to 1-2 with HCl. The acidified solution was loaded onto a hydrophobic resin (Diaion Sepabeads SP70) and the resin was washed with 10% ethanol in water (vol/vol) acidified to pH<2 with HCl followed by a wash with pure water to desalt the MCQAs and DCQAs. The compounds were eluted with 70% ethanol in water and the ethanol was evaporated from the eluent solution. This solution was decolored via membrane ultrafiltration (3 kDa nominal molecular weight cutoff, TurboClean NP010). The decolored permeate was concentrated then lyophilized to dryness to provide a stabilizer.

Acid-stability measurements were taken for samples of aspartame, SGMAs, and a combination of SGMAs with the stabilizer. The sample including SGMAs and the stabilizer had a weight ratio of SGMAs to MCQAs and DCQAs of 1:1. Acid-stability was measured in water having a pH of 1.7. The concentration of the aspartame or the SGMAs in the samples during the testing was 0.1 to 10 wt %. The samples were stored at room temperature (nominally about 22° C.) and samples were taken periodically. The concentration of the aspartame, SGMAs, MCQAs and DCQAs, as the case may be, was measured by UHPLC/UV then divided by the original concentration to determine a percent recovered.

FIG. 1 illustrates the results for three samples—one had 3000 ppm (0.3 wt %) aspartame, another had 5 wt % SGMAs, and the third had 5 wt % each of the SGMAs and the stabilizer. Aspartame has limited solubility, but 3000 ppm is on par with concentrations of throw syrups used to make some diet carbonated soft drinks that have about 500 ppm of aspartame. Acid-stability of the SGMAs alone fell well short of that of aspartame under these conditions. After 14 days of storage, the concentration of aspartame was about 78% of the initial concentration; stated another way, about 22% of the aspartame was degraded. In the same 14 days, the concentration of SGMAs in the SGMA-only sample was about 67% of the initial concentration, a degradation of about 33%. That means the SGMA degradation was 50% higher than the aspartame degradation (33% vs 22%).

In contrast, the SGMA concentration in the sample with SGMAs and stabilizer at 14 days was about 81% of the initial concentration, a degradation of 19%, which is almost 15% lower than the degradation of aspartame (19% vs 22%). The remarkable effects of the stabilized SGMAs continued to be borne out over the rest of the 35-day test, with more than 60% of the SGMAs remaining with the stabilizer versus only about 38% SGMAs remaining in the SGMA-only sample.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a composition comprising:
one or more steviol glycoside malonic acid esters (SGMAs) or salts thereof; and
a stabilizer comprising one or more caffeoyl-substituted quinic acids or salts thereof (e.g., the stabilizer can be chosen from 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, salts thereof, and combinations thereof).

Embodiment 2 provides the composition of Embodiment 1, wherein the stabilizer is one or more monocaffeoylquinic acids, dicaffeoylquinic acids, salts thereof, or a combination thereof.

Embodiment 3 provides the composition of Embodiment 2, wherein the stabilizer is a mixture of:
one or more monocaffeoylquinic acids, salts thereof, or a combination thereof; and
one or more dicaffeoylquinic acids, salts thereof, or a combination thereof.

Embodiment 4 provides the composition of any one of Embodiments 2-3, wherein the monocaffeoylquinic acid is one or more of 3-O-caffeoylquinic acid, 4-O-caffeoylquinic acid, or 5-O-caffeoylquinic acid.

Embodiment 5 provides the composition of any one of Embodiments 2-4, wherein the monocaffeoylquinic acid salt is one or more of a salt of 3-O-caffeoylquinic acid, a salt of 4-O-caffeoylquinic acid, or a salt of 5-O-caffeoylquinic acid.

Embodiment 6 provides the composition of any one of Embodiments 2-5, wherein the dicaffeoylquinic acid is one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, or 4,5-dicaffeoylquinic acid.

Embodiment 7 provides the composition of any one of Embodiments 2-6, wherein the dicaffeoylquinic acid salt is one or more of a salt of 1,3-dicaffeoylquinic acid, a salt of 1,4-dicaffeoylquinic acid, a salt of 1,5-dicaffeoylquinic acid, a salt of 3,4-dicaffeoylquinic acid, a salt of 3,5-dicaffeoylquinic acid, or a salt of 4,5-dicaffeoylquinic acid.

Embodiment 8 provides the composition of any one of Embodiments 2-7, wherein the salt of the monocaffeoylquinic acid or the salt of the dicaffeoylquinic acid comprises a counterion that is sodium, potassium, calcium, magnesium, ammonium, or a combination thereof.

Embodiment 9 provides the composition of any one of Embodiments 2-8, wherein the salt of the monocaffeoylquinic acid or the salt of the dicaffeoylquinic acid comprises a counterion that is sodium, potassium, or a combination thereof.

Embodiment 10 provides the composition of any one of Embodiments 1-9, wherein the malonic acid ester group has the structure:

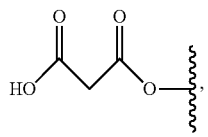

or a salt thereof.

Embodiment 11 provides the composition of any one of Embodiments 1-10, wherein the SGMA comprises one or more of glucose, xylose, rhamnose, or a combination thereof.

Embodiment 12 provides the composition of any one of Embodiments 1-11, wherein the SGMA has 1 to 3 malonic acid ester groups.

Embodiment 13 provides the composition of any one of Embodiments 1-12, wherein the SGMA has 1 malonic acid ester group.

Embodiment 14 provides the composition of any one of Embodiments 1-13, wherein the salt of the SGMA is a malonic acid salt comprising a counterion that is sodium, potassium, calcium, magnesium, ammonium, or a combination thereof.

Embodiment 15 provides the composition of any one of Embodiments 1-14, wherein the salt of the SGMA is a malonic acid salt comprising a counterion that is sodium, potassium, or a combination thereof.

Embodiment 16 provides the composition of any one of Embodiments 1-15, wherein the SGMA has the structure:

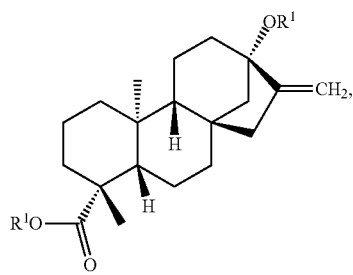

or a salt thereof;
wherein
at each occurrence $R^1$ is independently chosen from —H, a malonic acid ester or a salt thereof, and a glycosidically-bonded primary sugar,
at each occurrence the primary sugar is independently chosen from glucose, xylose, and rhamnose, and at each occurrence the primary sugar independently optionally comprises a secondary sugar glycosidically-bonded to the primary sugar, a malonic acid ester or a salt thereof bonded to the primary sugar, or a combination thereof,
at each occurrence the secondary sugar, if present, is independently chosen from glucose, xylose, and rhamnose, and at each occurrence the secondary sugar independently optionally comprises a tertiary sugar glycosidically-bonded to the secondary sugar, a malonic acid ester or a salt thereof bonded to the secondary sugar, or a combination thereof,
at each occurrence the tertiary sugar, if present, is independently chosen from glucose, xylose, and rhamnose, and at each occurrence the tertiary sugar independently optionally comprises a malonic acid ester or a salt thereof bonded to the tertiary sugar, and
the SGMA comprises at least one of the primary sugars and at least one of the malonic acid ester groups or a salt thereof.

Embodiment 17 provides the composition of Embodiment 16, wherein the SGMA comprises at least one of the secondary sugars.

Embodiment 18 provides the composition of any one of Embodiments 16-17, wherein the SMGA comprises at least one of the tertiary sugars.

Embodiment 19 provides the composition of any one of Embodiments 1-18, wherein the SGMA has the structure:

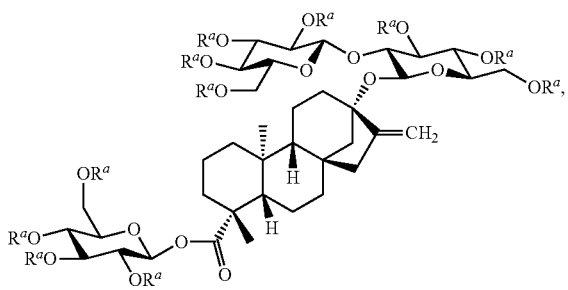

or a salt thereof;
wherein
at each occurrence $R^a$ is independently chosen from —H, a malonic acid ester or a salt thereof, and a sugar,
at each occurrence the sugar is independently chosen from glucose, xylose, and rhamnose,
at each occurrence the sugar independently optionally comprises a malonic acid ester or a salt thereof bonded to the sugar, and
the SGMA includes at least one malonic acid ester or a salt thereof.

Embodiment 20 provides the composition of Embodiment 19, wherein at each occurrence $R^a$ is independently chosen from —H and a malonic acid ester or a salt thereof.

Embodiment 21 provides the composition of any one of Embodiments 19-20, wherein the SGMA has the structure:

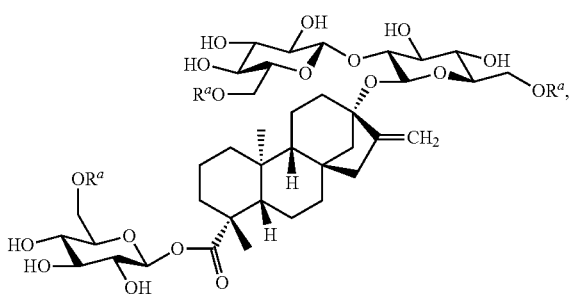

or a salt thereof.

Embodiment 22 provides the composition of any one of Embodiments 19-21, wherein the SGMA has the structure:

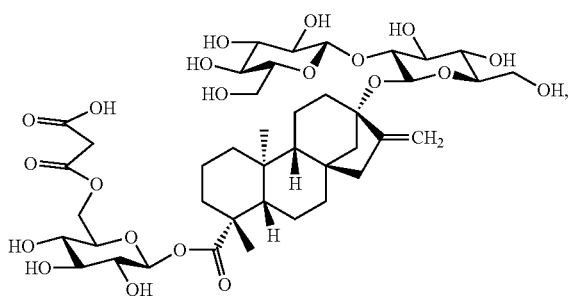

or a salt thereof.

Embodiment 23 provides the composition of any one of Embodiments 1-18, wherein the SGMA has the structure:

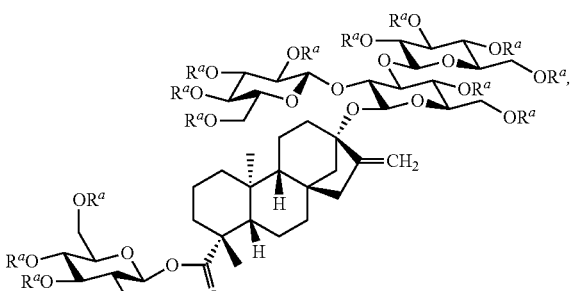

or a salt thereof;
wherein
- at each occurrence $R^a$ is independently chosen from —H, a malonic acid ester or a salt thereof, and a sugar,
- at each occurrence the sugar is independently chosen from glucose, xylose, and rhamnose,
- at each occurrence the sugar independently optionally comprises a malonic acid ester or a salt thereof bonded to the sugar, and
- the SGMA includes at least one malonic acid ester or a salt thereof.

Embodiment 24 provides the composition of Embodiment 23, wherein at each occurrence $R^a$ is independently chosen from —H and a malonic acid ester or a salt thereof.

Embodiment 25 provides the composition of any one of Embodiments 23-24, wherein the SGMA has the structure:

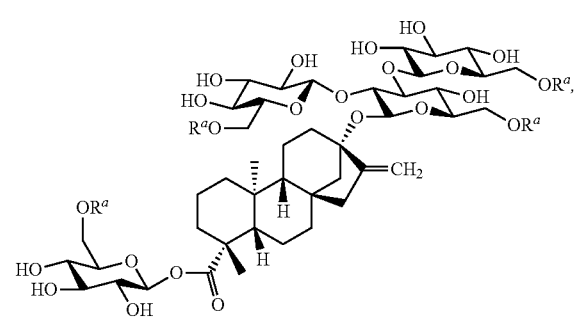

or a salt thereof.

Embodiment 26 provides the composition of any one of Embodiments 23-25, wherein the SGMA has the structure:

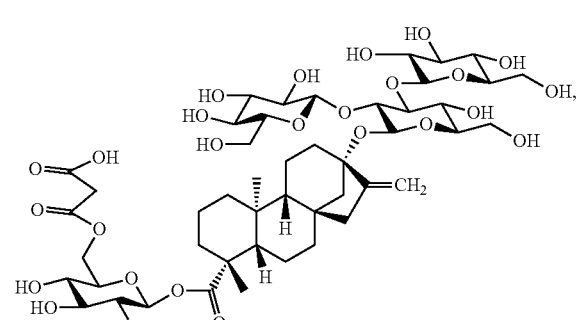

or a salt thereof.

Embodiment 27 provides the composition of any one of Embodiments 23-24, wherein the SGMA has the structure:

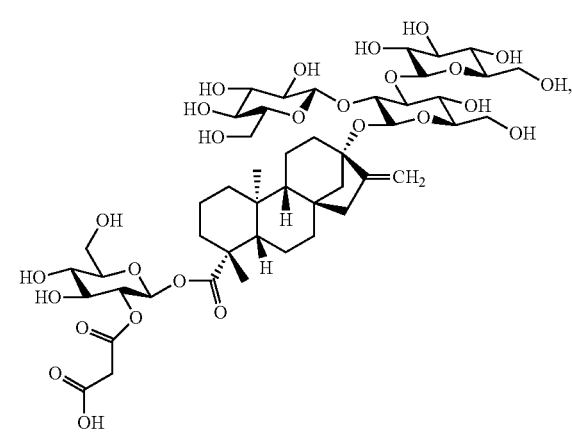

or a salt thereof.

Embodiment 28 provides the composition of any one of Embodiments 1-18, wherein the SGMA has the structure:

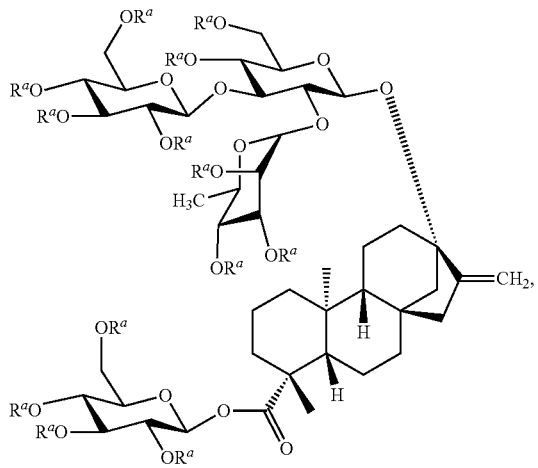

or a salt thereof;
wherein
at each occurrence $R^a$ is independently chosen from —H, a malonic acid ester or a salt thereof, and a sugar,
at each occurrence the sugar is independently chosen from glucose, xylose, and rhamnose,
at each occurrence the sugar independently optionally comprises a malonic acid ester or a salt thereof bonded to the sugar, and
the SGMA includes at least one malonic acid ester or a salt thereof.

Embodiment 29 provides the composition of Embodiment 28, wherein at each occurrence $R^a$ is independently chosen from —H and a malonic acid ester or a salt thereof.

Embodiment 30 provides the composition of any one of Embodiments 28-29, wherein the SGMA has the structure:

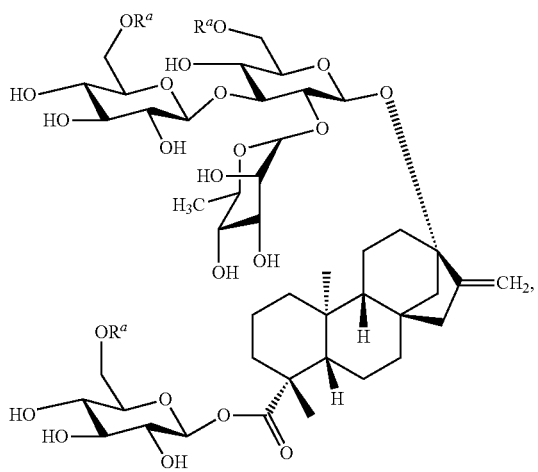

or a salt thereof.

Embodiment 31 provides the composition of any one of Embodiments 28-30, wherein the SGMA has the structure:

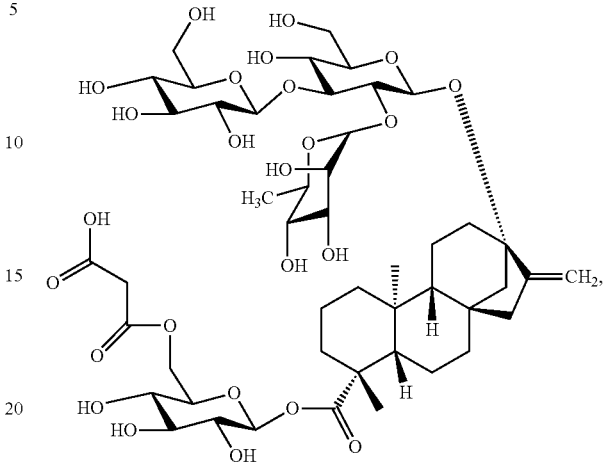

or a salt thereof.

Embodiment 32 provides the composition of any one of Embodiments 1-18, wherein the SGMA has the structure:

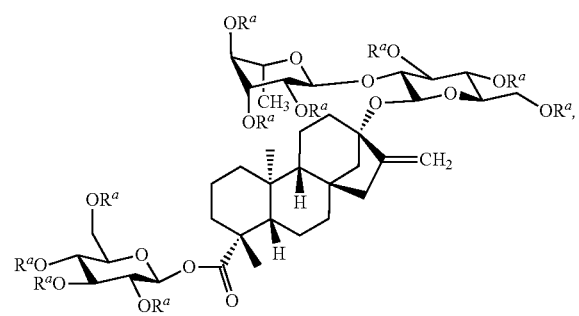

or a salt thereof;
wherein
at each occurrence $R^a$ is independently chosen from —H, a malonic acid ester or a salt thereof, and a sugar,
at each occurrence the sugar is independently chosen from glucose, xylose, and rhamnose,
at each occurrence the sugar independently optionally comprises a malonic acid ester or a salt thereof bonded to the sugar, and
the SGMA includes at least one malonic acid ester or a salt thereof.

Embodiment 33 provides the composition of Embodiment 32, wherein at each occurrence $R^a$ is independently chosen from —H and a malonic acid ester or a salt thereof.

Embodiment 34 provides the composition of any one of Embodiments 32-33, wherein the SGMA has the structure:

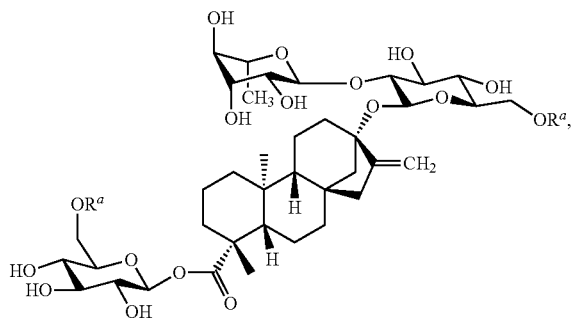

or a salt thereof.

Embodiment 35 provides the composition of any one of Embodiments 1-18, wherein the SGMA has the structure:

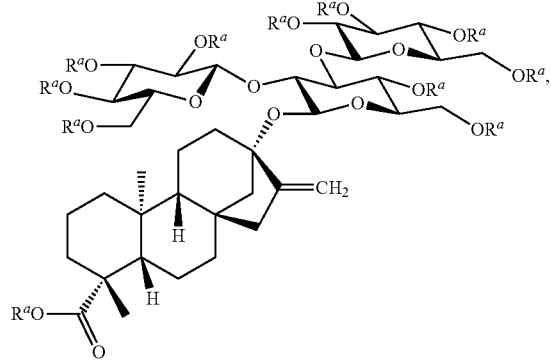

or a salt thereof;
wherein
- at each occurrence $R^a$ is independently chosen from —H, a malonic acid ester or a salt thereof, and a sugar,
- at each occurrence the sugar is independently chosen from glucose, xylose, and rhamnose,
- at each occurrence the sugar independently optionally comprises a malonic acid ester or a salt thereof bonded to the sugar, and
- the SGMA includes at least one malonic acid ester or a salt thereof.

Embodiment 36 provides the composition of Embodiment 35, wherein at each occurrence $R^a$ is independently chosen from —H and a malonic acid ester or a salt thereof.

Embodiment 37 provides the composition of any one of Embodiments 35-36, wherein the SGMA has the structure:

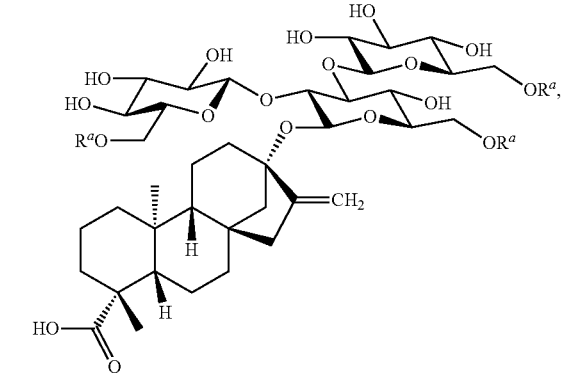

or a salt thereof.

Embodiment 38 provides the composition of any one of Embodiments 1-18, wherein the SGMA has the structure:

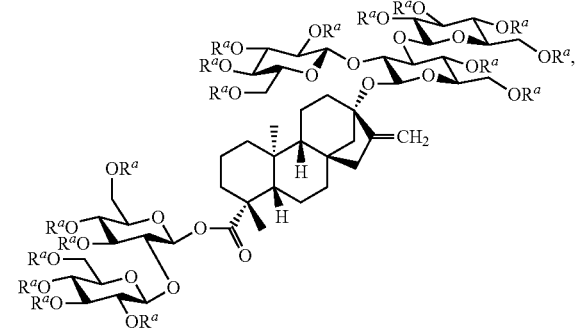

or a salt thereof;
wherein
- at each occurrence $R^a$ is independently chosen from —H, a malonic acid ester or a salt thereof, and a sugar,
- at each occurrence the sugar is independently chosen from glucose, xylose, and rhamnose,
- at each occurrence the sugar independently optionally comprises a malonic acid ester or a salt thereof bonded to the sugar, and
- the SGMA includes at least one malonic acid ester or a salt thereof.

Embodiment 39 provides the composition of Embodiment 38, wherein at each occurrence $R^a$ is independently chosen from —H and a malonic acid ester or a salt thereof.

Embodiment 40 provides the composition of any one of Embodiments 38-39, wherein the SGMA has the structure:

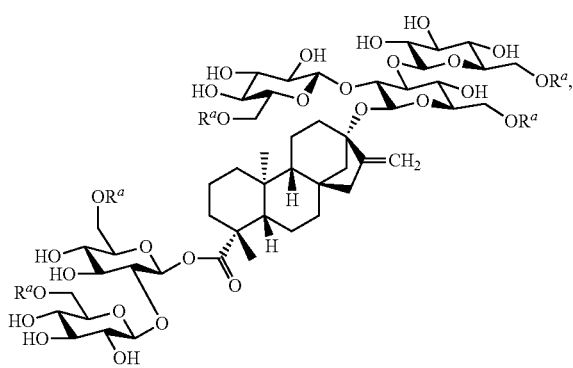

or a salt thereof.

Embodiment 41 provides the composition of any one of Embodiments 1-18, wherein the SGMA has the structure:

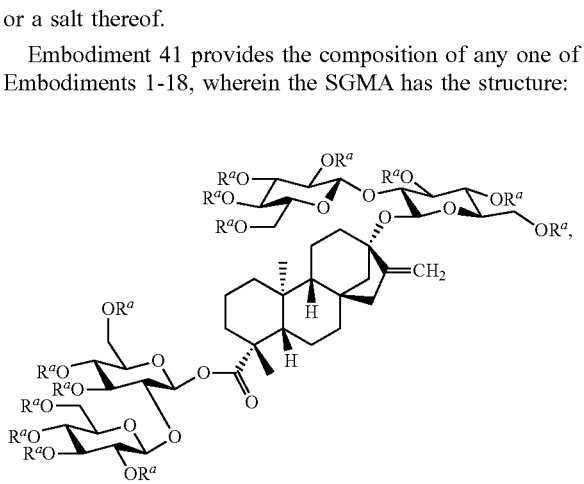

or a salt thereof;
wherein
at each occurrence R$^a$ is independently chosen from —H, a malonic acid ester or a salt thereof, and a sugar,
at each occurrence the sugar is independently chosen from glucose, xylose, and rhamnose,
at each occurrence the sugar independently optionally comprises a malonic acid ester or a salt thereof bonded to the sugar, and
the SGMA includes at least one malonic acid ester or a salt thereof.

Embodiment 42 provides the composition of Embodiment 41, wherein at each occurrence R$^a$ is independently chosen from —H and a malonic acid ester or a salt thereof.

Embodiment 43 provides the composition of any one of Embodiments 41-42, wherein the SGMA has the structure:

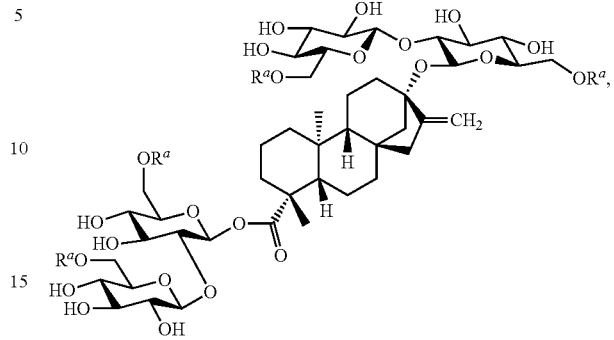

or a salt thereof.

Embodiment 44 provides the composition of any one of Embodiments 1-18, wherein the SGMA has the structure:

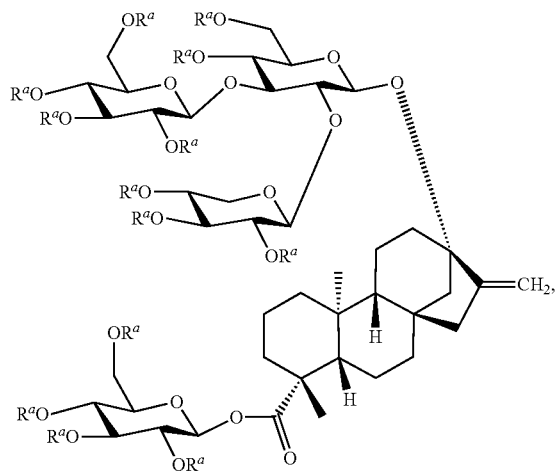

or a salt thereof;
wherein
at each occurrence R$^a$ is independently chosen from —H, a malonic acid ester or a salt thereof, and a sugar,
at each occurrence the sugar is independently chosen from glucose, xylose, and rhamnose,
at each occurrence the sugar independently optionally comprises a malonic acid ester or a salt thereof bonded to the sugar, and
the SGMA includes at least one malonic acid ester or a salt thereof.

Embodiment 45 provides the composition of Embodiment 44, wherein at each occurrence R$^a$ is independently chosen from —H and a malonic acid ester or a salt thereof.

Embodiment 46 provides the composition of any one of Embodiments 44-45, wherein the SGMA has the structure:

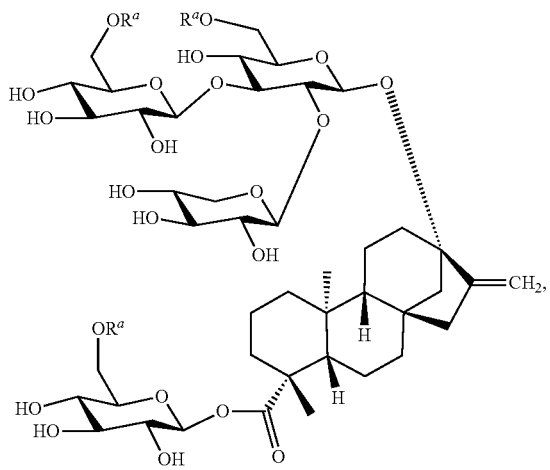

or a salt thereof.

Embodiment 47 provides the composition of any one of Embodiments 44-46, wherein the SGMA has the structure:

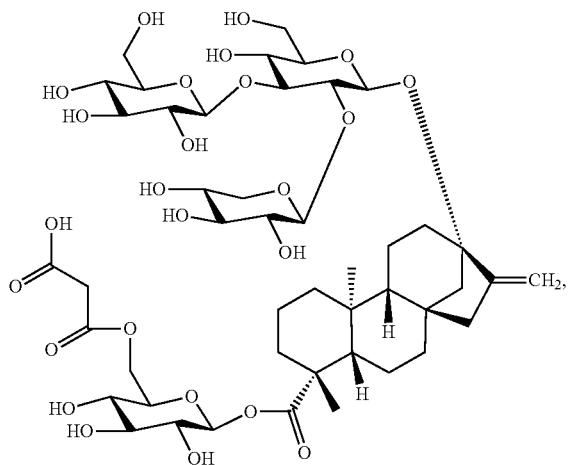

or a salt thereof.

Embodiment 48 provides the composition of any one of Embodiments 1-47, wherein the composition is substantially free of organic acid, citric acid, malic acid, phosphate, sulfate, colored bodies, chlorophyll, flavonoids, rutin, quercetin, quercitrin, glucose, fructose, amino acids, proteins, MCQAs, DCQAs, or a combination thereof.

Embodiment 49 provides the composition of any one of Embodiments 1-48, wherein the composition is substantially free of stevia plant matter that is not soluble in water, ethanol, or methanol.

Embodiment 50 provides the composition of any one of Embodiments 1-49, wherein the one or more SGMAs, salts thereof, or the combination thereof are 0.001 wt % to 99.999 wt % of the composition.

Embodiment 51 provides the composition of any one of Embodiments 1-50, wherein the one or more SGMAs, salts thereof, or the combination thereof are 5 wt % to 99.999 wt % of the composition.

Embodiment 52 provides the composition of any one of Embodiments 1-51, wherein the one or more SGMAs, salts thereof, or the combination thereof are 10 wt % to 99.999 wt % of the composition.

Embodiment 53 provides the composition of any one of Embodiments 1-52, wherein the one or more SGMAs, salts thereof, or the combination thereof are 0.01 wt % to 90 wt % of the composition.

Embodiment 54 provides the composition of any one of Embodiments 1-53, wherein the one or more SGMAs, salts thereof, or the combination thereof are 0.01 wt % to 30 wt % of the composition.

Embodiment 55 provides the composition of any one of Embodiments 1-54, wherein a mass ratio of the one or more SGMAs, salts thereof, or combination thereof, to the stabilizer is 0.1:1 to 10:1.

Embodiment 56 provides the composition of any one of Embodiments 1-55, wherein a mass ratio of the one or more SGMAs, salts thereof, or combination thereof to the stabilizer is 1:5 to 3:1.

Embodiment 57 provides the composition of any one of Embodiments 1-56, wherein the composition has a concentration of the one or more SGMAs, salts thereof, or combination thereof of 100 ppm to 500,000 ppm.

Embodiment 58 provides the composition of any one of Embodiments 1-57, wherein the composition has a concentration of the one or more SGMAs, salts thereof, or combination thereof of 200 ppm to 1,000 ppm.

Embodiment 59 provides the composition of any one of Embodiments 1-58, wherein the composition has a concentration of the one or more SGMAs, salts thereof, or combination thereof of 300 ppm to 700 ppm.

Embodiment 60 provides the composition of any one of Embodiments 1-59, wherein the composition has a concentration of the stabilizer of 100 ppm to 500,000 ppm.

Embodiment 61 provides the composition of any one of Embodiments 1-60, wherein the composition has a concentration of the stabilizer of 200 ppm to 1,000 ppm.

Embodiment 62 provides the composition of any one of Embodiments 1-61, wherein the composition has a concentration of the stabilizer of 300 ppm to 700 ppm.

Embodiment 63 provides the composition of any one of Embodiments 1-62, wherein the composition is substantially free of non-malonated steviol glycosides and salts thereof.

Embodiment 64 provides the composition of any one of Embodiments 1-63, wherein the composition further comprises one or more non-malonated steviol glycosides, salts thereof, or a combination thereof.

Embodiment 65 provides the composition of any one of Embodiments 1-64, wherein the composition has a ratio of non-malonated steviol glycosides, salts thereof, or a combination thereof to the one or more SGMAs of 0.001:1 to 1000:1.

Embodiment 66 provides the composition of any one of Embodiments 1-65, wherein the composition has a ratio of non-malonated steviol glycosides, salts thereof, or a combination thereof to the one or more SGMAs of 0.1:1 to 1000:1.

Embodiment 67 provides the composition of any one of Embodiments 1-66, wherein the composition has a ratio of non-malonated steviol glycosides, salts thereof, or a combination thereof to the one or more SGMAs of 2:1 to 1000:1.

Embodiment 68 provides the composition of any one of Embodiments 1-67, wherein the composition further comprises stevioside, rebaudioside A, rebaudioside C, dulcoside A, rebaudioside B, rebaudioside D, rebaudioside E, rebaudioside M, rebaudioside O, rebaudioside N, rebaudioside F, salts thereof, or a combination thereof.

Embodiment 69 provides the composition of any one of Embodiments 1-68, wherein the composition is an aqueous composition.

Embodiment 70 provides the composition of any one of Embodiments 1-69, wherein at least 20 wt % of the composition is water.

Embodiment 71 provides the composition of any one of Embodiments 1-70, wherein the composition has a pH of 1 to 9.

Embodiment 72 provides the composition of any one of Embodiments 1-71, wherein the composition has a pH of 1.7 to 4.

Embodiment 73 provides the composition of any one of Embodiments 1-72, wherein the composition has a pH of 2.5 to 3.5.

Embodiment 74 provides the composition of any one of Embodiments 1-73, wherein the composition has a pH of 1.7 to 2.0.

Embodiment 75 provides the composition of any one of Embodiments 1-74, wherein the composition has a solid form.

Embodiment 76 provides the composition of any one of Embodiments 1-75, wherein the composition is a freeze-dried powder.

Embodiment 77 provides the composition of any one of Embodiments 1-76, wherein the composition further comprises another stabilizer, a microbial stabilizer, another sweetener (e.g., other than the SMGAs or salts thereof), a bulking agent, erythritol, a desiccant, an anti-caking agent, or a combination thereof.

Embodiment 78 provides the composition of any one of Embodiments 1-77, wherein the SGMAs, salts thereof, or the combination thereof degrade more slowly over time at pH 1.7 to 4 as compared to a corresponding composition that comprises less or none of the stabilizer.

Embodiment 79 provides the composition of any one of Embodiments 1-78, wherein placing the composition at pH 1.7 over 5 days at 22° C. results in 90% or more of the SGMAs, salts thereof, or the combination thereof being undegraded.

Embodiment 80 provides the composition of any one of Embodiments 1-79, wherein placing the composition at pH 1.7 over 35 days at 22° C. results in 50% or more of the SGMAs, salts thereof, or the combination thereof being undegraded.

Embodiment 81 provides the composition of any one of Embodiments 1-80, wherein the composition has improved sweetness quality as compared to a corresponding composition that comprises less or none of the stabilizer.

Embodiment 82 provides the composition of any one of Embodiments 1-81, wherein the composition is a sweetener.

Embodiment 83 provides the composition of any one of Embodiments 1-82, wherein the composition is a throw syrup.

Embodiment 84 provides the composition of any one of Embodiments 1-83, wherein the composition is a sweetened beverage.

Embodiment 85 provides the composition of any one of Embodiments 1-84, wherein the composition is a chocolate milk, a tea, an energy drink, a drinkable yogurt, a flavored water, or a combination thereof.

Embodiment 86 provides the composition of any one of Embodiments 1-85, wherein the composition is a carbonated soft drink.

Embodiment 87 provides the composition of any one of Embodiments 1-86, wherein the composition is a solid food stuff.

Embodiment 88 provides the composition of any one of Embodiments 1-87, wherein the composition is a snack bar, a dried fruit product, a cookie, a cereal, a chocolate, a chewing gum, a candy, a cake, a donut, or a combination thereof.

Embodiment 89 provides the composition of any one of Embodiments 1-88, wherein the composition is a pharmaceutical composition, a nutritional supplement, a dental composition, or a combination thereof.

Embodiment 90 provides the composition of any one of Embodiments 1-89, wherein
  0-5% (wt) of the composition is one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin, or
  0-3% (wt) of the composition is one or more of malonate, malonic acid, oxalate, oxalic acid, lactate, lactic acid, succinate, succinic acid, malate, malic acid, citrate, and citric acid, or
  0-1% (wt) of the composition is one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol, or
  0-0.5% (wt) of the composition is one or more of tartrate, tartaric acid, pyruvate, pyruvic acid, fumarate, fumaric acid, ascorbic acid, sorbate, sorbic acid, acetate, acetic acid, and chlorophyll, or
  a combination thereof.

Embodiment 91 provides the composition of any one of Embodiments 1-90, wherein the composition comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

Embodiment 92 provides the composition of any one of Embodiments 1-91, wherein the composition is free of malonate, malonic acid, oxalate, oxalic acid, lactate, lactic acid, succinate, succinic acid, malate, and malic acid; or is free of pyruvate, pyruvic acid, fumarate, fumaric acid, tartrate, tartaric acid, sorbate, sorbic acid, acetate, and acetic acid; or is chlorophyll-free.

Embodiment 93 provides the composition of any one of Embodiments 1-92, wherein less than 0.1 wt % of the composition is one or more of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, *psyllium* husk mucilage, resistant starches, tara gum, tragacanth gum, xanthan gum, cellulose, chitin, and chitosan.

Embodiment 94 provides a beverage or beverage concentrate comprising:
- one or more steviol glycoside malonic acid esters (SGMAs) or salts thereof; and
- a stabilizer comprising one or more caffeoyl-substituted quinic acids or salts thereof (e.g., the stabilizer can be a mixture of one or more monocaffeoylquinic acids, salts thereof, or a combination thereof, and one or more dicaffeoylquinic acids, and salts thereof, or a combination thereof);
- wherein
  - the beverage or beverage concentrate has a pH of 1.7 to 4, and/or
  - a mass ratio of the one or more SGMAs, salts thereof, or combination thereof to the stabilizer is 1:5 to 3:1.

Embodiment 95 provides a method of making a composition comprising one or more steviol glycoside malonic acid esters (SGMAs) or salts thereof and a stabilizer comprising one or more caffeoyl-substituted quinic acids or salts thereof, the method comprising:
- combining a SGMA component comprising the one or more SGMAs, salts thereof, or combination thereof with the stabilizer to form the composition comprising one or more steviol glycoside malonic acid esters (SGMAs) or salts thereof and a stabilizer comprising one or more caffeoyl-substituted quinic acids or salts thereof, wherein
  - 0-5% (wt) of the SGMA component is one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin, or
  - 0-3% (wt) of the SGMA component is one or more of malonate, malonic acid, oxalate, oxalic acid, lactate, lactic acid, succinate, succinic acid, malate, malic acid, citrate, and citric acid, or
  - 0-1% (wt) of the SGMA component is one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol, or
  - 0-0.5% (wt) of the SGMA component is one or more of tartrate, tartaric acid, pyruvate, pyruvic acid, fumarate, fumaric acid, ascorbic acid, sorbate, sorbic acid, acetate, acetic acid, and chlorophyll, or
  - a combination thereof.

Embodiment 96 provides the method of Embodiment 95, wherein the SGMA component comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

Embodiment 97 provides the method of any one of Embodiments 95-96, wherein the SGMA component is free of malonate, malonic acid, oxalate, oxalic acid, lactate, lactic acid, succinate, succinic acid, malate, and malic acid; or is free of pyruvate, pyruvic acid, fumarate, fumaric acid, tartrate, tartaric acid, sorbate, sorbic acid, acetate, and acetic acid; or is chlorophyll-free.

Embodiment 98 provides the method of any one of Embodiments 95-97, wherein less than 0.1 wt % of the SGMA component is one or more of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, *psyllium* husk mucilage, resistant starches, tara gum, tragacanth gum, xanthan gum, cellulose, chitin, and chitosan.

Embodiment 99 provides the method of any one of Embodiments 95-98, wherein the one or more steviol glycoside malonic acid esters (SGMAs) or salts thereof and the one or more caffeoyl-substituted quinic acids or salts thereof are provided from separate sources (e.g., from different *stevia* leaf material).

Embodiment 100 provides a method of making a composition, the method comprising:
- combining an SGMA component with a stabilizer component, wherein
  - the SGMA component comprises at least 30 weight percent on a dry weight basis (wt % dwb) of one or more steviol glycoside malonic acid esters (SGMAs) or salts thereof, and
  - the stabilizer component comprises at least 30 wt % dwb of one or more caffeoyl-substituted quinic acids or salts thereof.

Embodiment 101 provides the method of Embodiment 100, wherein the composition is a beverage or beverage concentrate, the method further comprising combining the SGMA component and the stabilizer component in an aqueous solution having a pH of 1 to 6.

Embodiment 102 provides the method of Embodiment 101, wherein the SGMA component and the stabilizer component are combined before they are added to the aqueous solution.

Embodiment 103 provides the method of any one of Embodiments 100-102, wherein:
- 0-5% (wt) of the SGMA component, the stabilizer component, or both the SGMA component and the stabilizer component, is one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin, or
- 0-3% (wt) of the SGMA component, the stabilizer component, or both the SGMA component and the stabilizer component, is one or more of malonate, malonic acid, oxalate, oxalic acid, lactate, lactic acid, succinate, succinic acid, malate, malic acid, citrate, and citric acid, or 0-1% (wt) of the SGMA component, the stabilizer component, or both the SGMA component and the stabilizer component, is one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol, or 0-0.5% (wt) of the SGMA component, the stabilizer component, or both the SGMA component and the stabilizer component, is one or more of tartrate, tartaric acid, pyruvate, pyruvic acid, fumarate, fumaric acid, ascorbic acid, sorbate, sorbic acid, acetate, acetic acid, and chlorophyll.

Embodiment 104 provides the method of any one of Embodiments 100-103 wherein the SGMA component, the stabilizer component, or both the SGMA component and the stabilizer component comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

Embodiment 105 provides the method of any one of Embodiments 100-104, wherein the SGMA component, the stabilizer component, or both the SGMA component and the stabilizer component is free of malonate, malonic acid, oxalate, oxalic acid, lactate, lactic acid, succinate, succinic acid, malate, and malic acid; or is free of pyruvate, pyruvic acid, fumarate, fumaric acid, tartrate, tartaric acid, sorbate, sorbic acid, acetate, and acetic acid; or is chlorophyll-free.

Embodiment 106 provides the method of any one of Embodiments 100-105, wherein less than 0.1 wt % of the SGMA component, the stabilizer component, or both the SGMA component and the stabilizer component is one or more of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, *psyllium* husk mucilage, resistant starches, tara gum, tragacanth gum, xanthan gum, cellulose, chitin, and chitosan.

Embodiment 107 provides the composition, beverage or beverage concentrate, or method of any one or any combination of Embodiments 1-106 optionally configured such that all elements or options recited are available to use or select from.

The invention claimed is:

1. A composition comprising:
   one or more steviol glycoside malonic acid esters (SGMAs) or salts thereof; and
   a stabilizer comprising one or more caffeoyl-substituted quinic acids or salts thereof;
   wherein the composition is a beverage or beverage concentrate having a pH of 1.7 to 4; and
   wherein the SGMA or salt thereof has the structure:

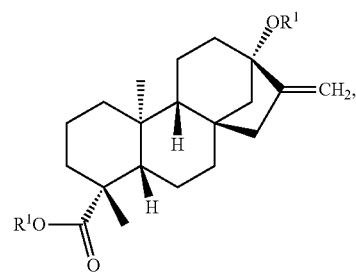

or a salt thereof;
wherein
at each occurrence $R^1$ is independently chosen from —H, and a glycosidically-bonded primary sugar,
at each occurrence the primary sugar is independently chosen from glucose, xylose, and rhamnose, and at each occurrence the primary sugar independently optionally comprises a secondary sugar glycosidically-bonded to the primary sugar, a malonic acid ester or a salt thereof bonded to the primary sugar, or a combination thereof,
at each occurrence the secondary sugar, if present, is independently chosen from glucose, xylose, and rhamnose, and at each occurrence the secondary sugar independently optionally comprises a tertiary sugar glycosidically-bonded to the secondary sugar, a malonic acid ester or a salt thereof bonded to the secondary sugar, or a combination thereof,
at each occurrence the tertiary sugar, if present, is independently chosen from glucose, xylose, and rhamnose, and at each occurrence the tertiary sugar independently optionally comprises a malonic acid ester or a salt thereof bonded to the tertiary sugar, and
the SGMA comprises at least one of the primary sugars and at least one of the malonic acid ester groups or a salt thereof on one or more of the primary, secondary, and tertiary sugars.

2. The composition of claim 1, wherein a mass ratio of the one or more SGMAs, salts thereof, or combination thereof, to the stabilizer is 0.1:1 to 10:1.

3. A composition comprising:
   one or more steviol glycoside malonic acid esters (SGMAs) or salts thereof; and
   a stabilizer comprising one or more caffeoyl-substituted quinic acids or salts thereof;
   wherein the composition has a mass ratio of the one or more SGMAs, salts thereof, or combination thereof to the stabilizer of 1:5 to 3:1, and
   wherein the SGMA or salt thereof has the structure:

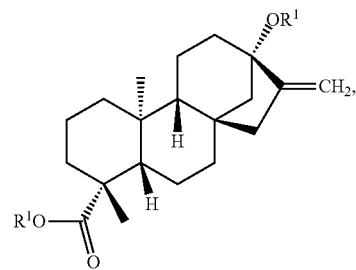

or a salt thereof;
wherein
at each occurrence $R^1$ is independently chosen from —H, and a glycosidically-bonded primary sugar,
at each occurrence the primary sugar is independently chosen from glucose, xylose, and rhamnose, and at each occurrence the primary sugar independently optionally comprises a secondary sugar glycosidically-bonded to the primary sugar, a malonic acid ester or a salt thereof bonded to the primary sugar, or a combination thereof,
at each occurrence the secondary sugar, if present, is independently chosen from glucose, xylose, and rhamnose, and at each occurrence the secondary sugar independently optionally comprises a tertiary sugar glycosidically-bonded to the secondary sugar, a malonic acid ester or a salt thereof bonded to the secondary sugar, or a combination thereof,
at each occurrence the tertiary sugar, if present, is independently chosen from glucose, xylose, and rhamnose, and at each occurrence the tertiary sugar independently optionally comprises a malonic acid ester or a salt thereof bonded to the tertiary sugar, and
the SGMA comprises at least one of the primary sugars and at least one of the malonic acid ester groups or a salt thereof on one or more of the primary, secondary, and tertiary sugars.

4. The composition of claim 3, wherein the composition is a sweetener, a throw syrup, a sweetened beverage, a carbonated soft drink, a solid food stuff, a pharmaceutical composition, a nutritional supplement, a dental composition, or a combination thereof.

5. The composition of claim 1, wherein the one or more caffeoyl-substituted quinic acids or salts thereof is chosen from 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, salts thereof, and combinations thereof.

6. The composition of claim 1, wherein the one or more caffeoyl-substituted quinic acids or salts thereof is one or more monocaffeoylquinic acids, dicaffeoylquinic acids, salts thereof, or a combination thereof.

7. The composition of claim 1, wherein the one or more caffeoyl-substituted quinic acids or salts thereof is a mixture of:
one or more monocaffeoylquinic acids, salts thereof, or a combination thereof; and
one or more dicaffeoylquinic acids, salts thereof, or a combination thereof.

8. The composition of claim 6, wherein the monocaffeoylquinic acid is one or more of 3-O-caffeoylquinic acid, 4-O-caffeoylquinic acid, or 5-O-caffeoylquinic acid.

9. The composition of claim 6, wherein the monocaffeoylquinic acid salt is one or more of a salt of 3-O-caffeoylquinic acid, a salt of 4-O-caffeoylquinic acid, or a salt of 5-O-caffeoylquinic acid.

10. The composition of claim 6, wherein the dicaffeoylquinic acid is one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, or 4,5-dicaffeoylquinic acid.

11. The composition of claim 6, wherein the dicaffeoylquinic acid salt is one or more of a salt of 1,3-dicaffeoylquinic acid, a salt of 1,4-dicaffeoylquinic acid, a salt of 1,5-dicaffeoylquinic acid, a salt of 3,4-dicaffeoylquinic acid, a salt of 3,5-dicaffeoylquinic acid, or a salt of 4,5-dicaffeoylquinic acid.

12. The composition of claim 1, wherein the one or more SGMAs, salts thereof, or the combination thereof are 10 wt % to 99.999 wt % of the composition.

13. The composition of claim 1, wherein the composition has a concentration of the stabilizer of 200 ppm to 1,000 ppm.

14. The composition of claim 1, wherein the SGMAs, salts thereof, or the combination thereof degrade more slowly over time at pH 1.7 to 4 as compared to a corresponding composition that comprises less or none of the stabilizer.

15. The composition of claim 1, wherein the composition has improved sweetness quality as compared to a corresponding composition that comprises less or none of the stabilizer.

16. A method of making a composition comprising one or more steviol glycoside malonic acid esters (SGMAs) or salts thereof and a stabilizer comprising one or more caffeoyl-substituted quinic acids or salts thereof, the method comprising:
combining a SGMA component comprising the one or more SGMAs, salts thereof, or combination thereof with the stabilizer to form the composition comprising one or more steviol glycoside malonic acid esters (SGMAs) or salts thereof and a stabilizer comprising one or more caffeoyl-substituted quinic acids or salts thereof, wherein
0-5% (wt) of the SGMA component is one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin, or
0-3% (wt) of the SGMA component is one or more of malonate, malonic acid, oxalate, oxalic acid, lactate, lactic acid, succinate, succinic acid, malate, malic acid, citrate, and citric acid, or
0-1% (wt) of the SGMA component is one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol, or
0-0.5% (wt) of the SGMA component is one or more of tartrate, tartaric acid, pyruvate, pyruvic acid, fumarate, fumaric acid, ascorbic acid, sorbate, sorbic acid, acetate, acetic acid, and chlorophyll, or a combination thereof; and
wherein the SGMA or salt thereof has the structure:

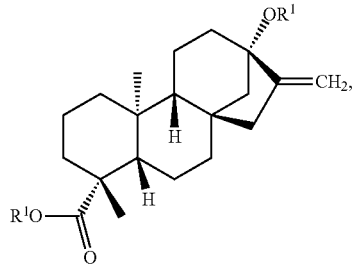

or a salt thereof;
wherein
at each occurrence $R^1$ is independently chosen from —H, and a glycosidically-bonded primary sugar,
at each occurrence the primary sugar is independently chosen from glucose, xylose, and rhamnose, and at each occurrence the primary sugar independently optionally comprises a secondary sugar glycosidically-bonded to the primary sugar, a malonic acid ester or a salt thereof bonded to the primary sugar, or a combination thereof,
at each occurrence the secondary sugar, if present, is independently chosen from glucose, xylose, and rhamnose, and at each occurrence the secondary sugar independently optionally comprises a tertiary sugar glycosidically-bonded to the secondary sugar, a malonic acid ester or a salt thereof bonded to the secondary sugar, or a combination thereof,
at each occurrence the tertiary sugar, if present, is independently chosen from glucose, xylose, and rhamnose, and at each occurrence the tertiary sugar independently optionally comprises a malonic acid ester or a salt thereof bonded to the tertiary sugar, and
the SGMA comprises at least one of the primary sugars and at least one of the malonic acid ester groups or a salt thereof on one or more of the primary, secondary, and tertiary sugars.

17. The method of claim 16, wherein the SGMA component comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

18. The method of claim 16, wherein the SGMA component is free of malonate, malonic acid, oxalate, oxalic acid, lactate, lactic acid, succinate, succinic acid, malate, and malic acid; or is free of pyruvate, pyruvic acid, fumarate, fumaric acid, tartrate, tartaric acid, sorbate, sorbic acid, acetate, and acetic acid; or is chlorophyll-free.

19. The method of claim 16, wherein less than 0.1 wt % of the SGMA component is one or more of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, psyllium husk mucilage, resistant starches, tara gum, tragacanth gum, xanthan gum, cellulose, chitin, and chitosan.

20. A method of making a composition, the method comprising:
combining an SGMA component with a stabilizer component, wherein
the SGMA component comprises at least 30 weight percent on a dry weight basis (wt % dwb) of one or more steviol glycoside malonic acid esters (SGMAs) or salts thereof, and
the stabilizer component comprises at least 30 wt % dwb of one or more caffeoyl-substituted quinic acids or salts thereof;
wherein the SGMA or salt thereof has the structure:

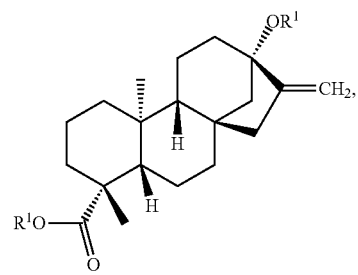

or a salt thereof;
wherein
at each occurrence $R^1$ is independently chosen from —H, and a glycosidically-bonded primary sugar,
at each occurrence the primary sugar is independently chosen from glucose, xylose, and rhamnose, and at each occurrence the primary sugar independently optionally comprises a secondary sugar glycosidically-bonded to the primary sugar, a malonic acid ester or a salt thereof bonded to the primary sugar, or a combination thereof,
at each occurrence the secondary sugar, if present, is independently chosen from glucose, xylose, and rhamnose, and at each occurrence the secondary sugar independently optionally comprises a tertiary sugar glycosidically-bonded to the secondary sugar, a malonic acid ester or a salt thereof bonded to the secondary sugar, or a combination thereof,
at each occurrence the tertiary sugar, if present, is independently chosen from glucose, xylose, and rhamnose, and at each occurrence the tertiary sugar independently optionally comprises a malonic acid ester or a salt thereof bonded to the tertiary sugar, and
the SGMA comprises at least one of the primary sugars and at least one of the malonic acid ester groups or a salt thereof on one or more of the primary, secondary, and tertiary sugars.

21. The method of claim 20, wherein the composition is a beverage or beverage concentrate, the method further comprising combining the SGMA component and the stabilizer component in an aqueous solution having a pH of 1 to 6.

22. The method of claim 21, wherein the SGMA component and the stabilizer component are combined before they are added to the aqueous solution.

23. The method of claim 20, wherein:
0-5% (wt) of the SGMA component, the stabilizer component, or both the SGMA component and the stabilizer component, is one or more of quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein, hesperidin, naringin, rutin, quercitrin, luteolin-glucoside, quercetin-xyloside, cyanidin, delphinidin, malvidin, pelargonidin, peonidin, and petunidin, or 0-3% (wt) of the SGMA component, the stabilizer component, or both the SGMA component and the stabilizer component, is one or more of malonate, malonic acid, oxalate, oxalic acid, lactate, lactic acid, succinate, succinic acid, malate, malic acid, citrate, and citric acid, or 0-1% (wt) of the SGMA component, the stabilizer component, or both the SGMA component and the stabilizer component, is one or more of sulfate, sulfuric acid, phosphate, phosphoric acid, nitrate, nitric acid, nitrite, nitrous acid, chloride, hydrochloric acid, ammonia, ammonium, tannic acid, monoglycerides, diglycerides, triglycerides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose, glycerol, sorbitol, mannitol, xylitol, maltitol, lactitol, erythritol, isomalt, and inositol, or 0-0.5% (wt) of the SGMA component, the stabilizer component, or both the SGMA component and the stabilizer component, is one or more of tartrate, tartaric acid, pyruvate, pyruvic acid, fumarate, fumaric acid, ascorbic acid, sorbate, sorbic acid, acetate, acetic acid, and chlorophyll.

24. The composition of claim 1, wherein the one or more SGMAs, salts thereof, or the combination thereof are 0.01 wt % to 30 wt % of the composition.

* * * * *